(12) United States Patent
Hasegawa et al.

(10) Patent No.: US 9,852,897 B2
(45) Date of Patent: Dec. 26, 2017

(54) HYBRID ION SOURCE, MASS SPECTROMETER, AND ION MOBILITY DEVICE

(71) Applicant: HITACHI HIGH-TECHNOLOGIES CORPORATION, Tokyo (JP)

(72) Inventors: Hideki Hasegawa, Tokyo (JP); Hiroyuki Satake, Tokyo (JP); Masao Suga, Tokyo (JP); Yuichiro Hashimoto, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 134 days.

(21) Appl. No.: 14/442,199

(22) PCT Filed: Nov. 7, 2013

(86) PCT No.: PCT/JP2013/080111
§ 371 (c)(1),
(2) Date: May 12, 2015

(87) PCT Pub. No.: WO2014/084015
PCT Pub. Date: Jun. 5, 2014

(65) Prior Publication Data
US 2016/0300703 A1    Oct. 13, 2016

(30) Foreign Application Priority Data

Nov. 29, 2012   (JP) .................................. 2012-261212

(51) Int. Cl.
*H01J 49/10*    (2006.01)
*G01N 27/62*    (2006.01)
*H01J 49/16*    (2006.01)

(52) U.S. Cl.
CPC ............ *H01J 49/107* (2013.01); *G01N 27/62* (2013.01); *H01J 49/165* (2013.01); *H01J 49/168* (2013.01)

(58) Field of Classification Search
CPC ...... H01J 49/168; H01J 49/165; H01J 49/107; G01N 30/726; G01N 30/7266
See application file for complete search history.

(56) References Cited

U.S. PATENT DOCUMENTS 6,635,868 B2 * 10/2003 Shiokawa ............. H01J 49/107
                                                    250/288
6,639,215 B2    10/2003 Takada et al.
(Continued)

FOREIGN PATENT DOCUMENTS

EP       1 739 720 A2   1/2007
JP       4553011 B2     9/2010
(Continued)

OTHER PUBLICATIONS

Extended European Search Report received in corresponding European Application No. 13858963.5 dated Jun. 20, 2016.

*Primary Examiner* — Wyatt Stoffa
(74) *Attorney, Agent, or Firm* — Mattingly & Malur, PC

(57) ABSTRACT

Provided is an ion source achieving high sensitivity and high robustness while executing a plurality of types of ionization schemes. To this end, a hybrid ion source (1) includes: a chamber (24); a first ion source (2) to spray a sample solution (5) for ionization; a second ion source (3) to ionize droplets and/or a gas component sprayed from the first ion source (2); a first electrode (11) to introduce a first ion (7) generated by the first ion source (2), and a second ion generated by the second ion source (3); and an exhaust pump (27) that generates air flow (26) in a direction from a first space area (23) where the first ion (7) is generated to a
(Continued)

second space area (19) in the second ion source (3) where the second ion is generated.

20 Claims, 22 Drawing Sheets

(56) References Cited

U.S. PATENT DOCUMENTS

| | | | |
|---|---|---|---|
| 6,686,592 B1 | 2/2004 | Sakairi et al. | |
| 7,488,953 B2 | 2/2009 | Fischer et al. | |
| 2001/0022344 A1* | 9/2001 | Takada | G01N 30/7266 250/288 |
| 2004/0079881 A1* | 4/2004 | Fischer | H01J 49/0445 250/288 |
| 2004/0094702 A1* | 5/2004 | Clemmer | G01N 27/622 250/283 |
| 2006/0086908 A1* | 4/2006 | Fischer | H01J 49/06 250/423 R |
| 2007/0138406 A1* | 6/2007 | Mordehai | H01J 49/107 250/426 |
| 2008/0272285 A1* | 11/2008 | Giannantonio | G01N 27/622 250/281 |
| 2009/0236518 A1* | 9/2009 | Kobayashi | G01N 30/726 250/288 |
| 2011/0309243 A1* | 12/2011 | Whitehouse | H01J 49/0431 250/282 |
| 2012/0018632 A1* | 1/2012 | Whitehouse | H01J 49/045 250/287 |
| 2012/0104248 A1* | 5/2012 | Hardman | H01J 49/165 250/288 |
| 2014/0326871 A1* | 11/2014 | Whitehouse | H01J 49/0431 250/288 |

FOREIGN PATENT DOCUMENTS

| | | |
|---|---|---|
| WO | 2006/107831 A2 | 10/2006 |
| WO | 2007032088 A1 | 3/2007 |

* cited by examiner

HYBRID ION SOURCE, MASS SPECTROMETER, AND ION MOBILITY DEVICE

TECHNICAL FIELD

The present invention relates to a hybrid ion source including a plurality of types of ion sources based on different ionization schemes, and a mass spectrometer and an ion mobility spectrometer including such an ion source.

BACKGROUND ART

Atmospheric pressure ionization/mass spectrometers are configured to introduce ions generated at atmospheric pressure into a vacuum system to analyze the mass of the ions. Atmospheric pressure ionization includes electrospray ionization (ESI) (hereinafter called "ESI") and atmospheric pressure chemical ionization (APCI) (hereinafter called "APCI"), for example.

The ESI is a technique of passing a sample solution through a capillary, to which high voltage is applied, for spraying to generate charged droplets, and creating ions through repetitive evaporation and breakup of these charged droplets. The ESI is an ionization scheme capable of treating a high-molecular weight sample, a highly-polar sample or the like. In the ESI, a technique of spraying a large amount of heated gas is typically used in combination to promote evaporation and vaporization of the droplets.

The APCI is a technique of heating a sample solution for vaporization, and ionizing the obtained solvent molecules through corona discharge. In the case of this technique, electrical charge is transferred between the primary ions generated by the corona discharge and sample molecules, whereby the sample molecules are ionized. The APCI can be used for a low-molecular weight sample having a smaller molecular weight or a low-polarity sample having smaller polarity than the ESI.

Patent Literature 1 and Patent Literature 2 describe a technique of improving the performance of the APCI. In this technique, the direction of introducing sample gas obtained by vaporization of a sample solution into a corona discharge area and the ion traveling direction are inverted. This lowers the reaction efficiency between the primary ions generated by the corona discharge and an inhibitory factor present in the atmosphere. As a result, generation of noise ions can be suppressed. This also can improve the reaction efficiency between the primary ions and the sample molecules, and so increase the detected intensity of generated ions.

When such ionization schemes treating different samples and being based on different principles (e.g., the ESI and the APCI) can be implemented with one ion source, then the range of substances to be measured and the application range of the ion source can be expanded. The present specification refers to the ion source supporting a plurality of types of ionization schemes as a hybrid ion source.

CITATION LIST

Patent Literatures

Patent Literature 1: U.S. Pat. No. 6,686,592 B
Patent Literature 2: U.S. Pat. No. 6,639,215 B
Patent Literature 3: JP 4553011 B
Patent Literature 4: U.S. Pat. No. 7,488,953 B

SUMMARY OF INVENTION

Technical Problem

Patent Literature 1 discloses the ion source for the APCI. Patent Literature 1, however, does not describe the use of the APCI and the ESI in combination.

Like Patent Literature 1, Patent Literature 2 also discloses the ion source for the APCI. This document, however, does not describe the use of the APCI and the ESI in combination. Patent Literature 2 discloses the technique of heating a sample solution at an upstream part of the sample introducing tube for vaporization, which is then introduced to an ionization part. Note here that the ESI is a technique of generating ions from a solution, and so ions cannot be generated from sample gas supplied. This means that the ESI that is based on the supplying of a sample solution cannot be combined with the APCI.

Patent Literature 3 proposes the scheme of implementing ionization by the ESI and ionization by the APCI using one ion source. According to Patent Literature 3, an electrostatic spray by the ESI and a needle electrode by the APCI are disposed in the same space, where ionization by the ESI and ionization by the APCI are carried out simultaneously. This scheme, however, has a problem of mutually adverse effects between high voltage applied to the electrostatic spray and high voltage applied to the needle electrode so as to mutually lower the ion intensity.

Patent Literature 4 also discloses the technique of disposing an electrostatic spray by the ESI and a needle electrode by the APCI in the same space, where ionization by the ESI and ionization by the APCI are carried out simultaneously. According to the technique disclosed by Patent Literature 4, a shield electrode is disposed between the electrostatic spray and the needle electrode to suppress influences from the other electric field. The shield electrode physically separates the space in the chamber into two areas (the ESI area and the APCI area). This prevents sample gas supplied to the ESI area by spraying from the electrostatic spray from being introduced to the APCI area beyond the shield electrode. The technique described in Patent Literature 4 has therefore a concern of lowering in ion intensity generated by the APCI.

In this way, although an ion source supporting both of the ESI and the APCI has been proposed, these conventional schemes can achieve only low ion intensity through simultaneous implementation of the ESI and the APCI. A single ionization mode is therefore still used typically for the analysis requiring high sensitivity.

Then the present invention provides a hybrid ion source achieving high sensitivity and high robustness while carrying out a plurality of types of ionization schemes simultaneously.

Solution to Problem

To solve the above problems, a hybrid ion source according to the present invention includes: a chamber; a first ion source to spray a sample solution for ionization; a second ion source to ionize droplets and/or a gas component sprayed from the first ion source; a first electrode to introduce a first ion generated by the first ion source, and a second ion generated by the second ion source; and exhaust means that generates air flow in a direction from a first space area where the first ion is generated to a second space area in the second ion source where the second ion is generated.

Advantageous Effects of Invention

The present invention realizes a hybrid ion source achieving both of high sensitivity for ion analysis and high robustness to support various ionization schemes while carrying out the plurality of types of ionization schemes simultaneously. Problems, configurations, and advantageous effects other than those described above will be made clear by the following description of embodiments.

DESCRIPTION OF EMBODIMENTS

The following describes embodiments of the present invention with reference to the drawings. Embodiments of the present invention are not limited to the below-described examples, and can be modified variously within the scope of its technical idea.

Embodiment 1

The present embodiment describes a hybrid ion source including an ESI ion source and an APCI ion source. The present embodiment describes the hybrid ion source having the following features (a) to (c):

(a) an ESI ion source and an APCI ion source are disposed so as to have a mutually orthogonal positional relationship;

(b) the APCI ion source and a first aperture electrode as an ion outlet are disposed so as to have a mutually opposed positional relationship; and (c) an exhaust pump is disposed at the APCI ion source so as to generate an air flow from the ESI ionization area to a corona discharge area.

Figure 1:
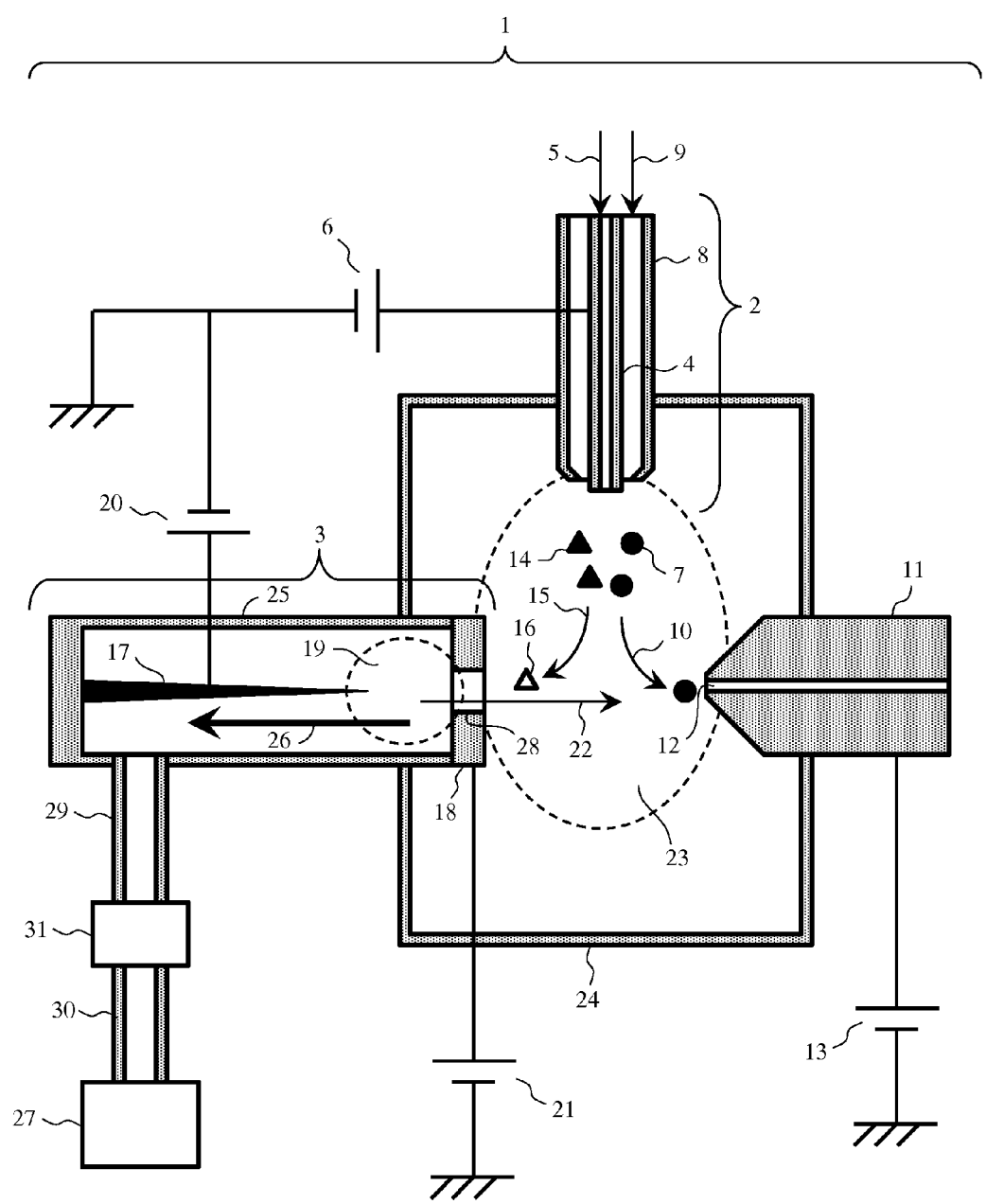
FIG. 1 illustrates a configuration of a hybrid ion source according to Embodiment 1.

FIG. 1 illustrates an exemplary configuration of a hybrid ion source 1 according to the present embodiment. The hybrid ion source 1 includes an ESI ion source 2 and an APCI ion source 3.

In the case of the present embodiment, the ESI ion source 2 is disposed at the ceiling face of an ESI ionization chamber 24 (chamber) so that its blow-out direction is directed vertically downward. The APCI ion source 3 is disposed in the direction perpendicular to the side wall of the ESI ionization chamber 24 (chamber). That is, they are disposed so that the ion blow-out direction of the ESI ion source 2 and the ion blow-out direction of the APCI ion source 3 are mutually orthogonal.

The blow-out port of the APCI ion source 3 and an opening 12 of a first aperture electrode 11 as the ion outlet (introduction port of ions to a mass spectrometry/detection unit) are disposed so as to be mutually opposed. The opening 12 at the forward end of the first aperture electrode 11 is disposed in an expected angle of a cone-shaped ion orbit emitted from the opening of the APCI ion source 3 or in the range of the vicinity thereof. Such an arrangement allows APCI ions to be introduced from the opening 12 to the first aperture electrode 11 effectively.

The ESI ion source 2 has a capillary 4, to which high voltage is applied from a power source 6 while passing a sample solution 5 through the capillary. This makes the sample solution 5 to be electrostatic-sprayed from the forward end of the capillary 4. A part of the sample solution 5 electrostatic-sprayed repeats evaporation and breakup to be ESI ions 7. The value of high voltage applied to the capillary 4 is typically a few kV (absolute value). In order to generate positive ions, voltage at +a few kV is applied to the capillary 4. In order to generate negative ions, voltage at −a few kV is applied to the capillary 4.

The capillary 4 typically has an inner diameter set at 1 mm or less. The flow rate of the sample solution 5 depends on the inner diameter of the capillary 4. The flow rate of the sample solution 5 is typically set in the range from the order of nL/min to the order of mL/min.

In the case of the present embodiment, a spray pipe 8 is disposed so as to surround the circumference of the capillary 4, and nebulizer gas 9 is introduced between the capillary 4 and the spray pipe 8. The nebulizer gas 9 introduced promotes vaporization of the sample solution 5 sprayed from the capillary 4. The nebulizer gas 9 typically used is inert gas, such as nitrogen. The typical flow rate of the nebulizer gas 9 is set in the range of about 0.1 L/min to 10 L/min. When the inner diameter of the capillary 4 is very small or the flow rate of the sample solution 5 is very small, the setting of the spray pipe 8 and the introduction of the nebulizer gas 9 are not always required.

The ESI ions 7 (black circles) generated by the ESI ion source 2 pass through the orbit of arrow 10, for example, and then are introduced to the opening 12 of the first aperture electrode 11. Voltage up to about a few hundreds of V (absolute value) is applied from a power source 13 to the first aperture electrode 11. In order to generate positive ions, positive voltage is applied to the first aperture electrode 11, and in order to generate negative ions, negative voltage is applied to the first aperture electrode 11. Then, voltage of the power source 6 and voltage of the power source 13 are set so that ions generated are attracted to the side of the first aperture electrode 11.

As described above, the ESI ions 7 are generated by spraying the sample solution 5 from the forward end of the capillary 4, where a part of the sample solution 5 is not ionized and stays in the state of droplets 14 (black triangles). Some of the droplets 14 are charged, but have a large particle size as compared with ions or the like, and so are less affected from the electric field between the capillary 4 and the first aperture electrode 11 and are affected more from an air flow 26 formed by an exhaust pump 27. The droplets 14 pass along the orbit of arrow 15, for example. A part of the droplets 14 is vaporized in the course of traveling to be sample gas 16 (white triangle).

The sample gas 16 is introduced to the inside of the APCI ion source 3 via an opening 28 bored at a counter electrode 18. The APCI ion source 3 has a hollow enclosure, and has the counter electrode 18 attached to a first end side. An opening for exhaust is disposed on a second end side of the enclosure (opposite side of the first end side).

A needle electrode 17 is attached inside of the enclosure of the APCI ion source 3. The counter electrode 18 is paired with this needle electrode 17. In the enclosure, a corona discharge area 19 is defined at a space between the forward end of the needle electrode 17 and the counter electrode 18.

The needle electrode 17 is desirably made of metal and has a sharp forward end. For instance, it is desirably made of a material resistant to discharge or abrasion, such as tungsten. Such a type of material used can achieve longer life or improved durability of the needle electrode 17.

At the corona discharge area 19, solvent molecules in the sample gas 16 are ionized by corona discharge. That is, primary ions are generated. The solvent molecules depend on the solvent used for the sample solution 5. The solvent used includes organic solvent, water, mixture of them, or the like. The solvent mixing with additive, such as acid, may be used.

In order to generate corona discharge, high voltage at a few kV (absolute value) is applied to the needle electrode 17 from a power source 20. Voltage up to a few kV (absolute value) is then applied to the counter electrode 18 from a power source 21. In order to generate positive ions, voltage at +a few kV is applied to the needle electrode 17, and in order to generate negative ions, voltage at −a few kV is applied to the needle electrode 17.

Similar voltage to the needle electrode 17 is applied to the counter electrode 18 as well. That is, in order to generate positive ions, positive voltage is applied to the counter electrode 18, and in order to generate negative ions, negative voltage is applied to the counter electrode.

When primary ions are generated by corona discharge, then electrical charge is transferred between the primary ions generated and sample molecules in the sample gas 16, whereby sample ions (APCI ions) are generated. The thus generated APCI ions pass along the orbit of arrow 22, for example, and then are introduced to the opening 12 of the first aperture electrode 11. Such movement of the APCI ions is against the air flow 26.

The air flow 26 from the ESI ionization chamber 24 which defines an ESI ionization area 23 to a corona discharge chamber 25 which defines the corona discharge area 19 is generated by the exhaust pump 27. The exhaust pump 27 has an intake port connected to an opening formed at the second end side of the enclosure of the APCI ion source 3 via pipes 29 and 30.

The capacity of the exhaust pump 27 is up to about a few tens of L/min, which is adjusted by a flow-rate adjustment mechanism 31 disposed at some part along the pipes 29 and 30. The flow-rate adjustment mechanism 31 includes a flow controller, a valve or the like. When the exhaust pump 27 has a flow-rate adjustment function, or when the capacity of the exhaust pump 27 is the optimum flow rate, the flow-rate adjustment mechanism 31 is not essential.

In the case of the present embodiment, two divided areas of the ESI ionization area 23 and the corona discharge area 19 are defined by the counter electrode 18. Herein the counter electrode 18 has electrical potential set at the electrical potential applied from the power source 21. This can reduce the mutual influences on voltage applied to the capillary 4 of the ESI ion source 2 and voltage applied to the needle electrode 17 of the APCI ion source 3 from the other electric field.

As a result, lowering of intensity of ions generated at the ESI ion source 2 and the APCI ion source 3 can be prevented. Further since the air flow 26 occurs in the direction from the ESI ionization area 23 to the corona discharge area 19, the introducing efficiency of the sample gas 16 to the corona discharge area 19 can be improved. Due to such an increasing amount of the sample gas 16 introduced to the corona discharge area 19, the improvement of intensity of APCI ions generated also can be expected.

In the case of the present embodiment, the direction of introducing the sample gas 16 vaporized from the sample solution 5 and the traveling direction of the APCI ions (arrow 22) are inversed. This can lower the reaction efficiency of the primary ions generated by corona discharge with an inhibitory factor present in the atmosphere, and so can suppress the generation of noise ions and can improve the reaction efficiency of the primary ions and the sample molecules. As a result the detected intensity of the APCI ions can be further improved.

In the present embodiment, impurities at the corona discharge area 19 can be removed by the air flow 26, whereby stable ionization can be realized for a long time. That is, the robustness can be improved.

In the case of the present embodiment, the ESI ion source 2 and the APCI ion source 3 are disposed to have an orthogonal positional relationship, which can effectively suppress the situation where a component of the droplets 14 that travels straight ahead because of insufficient vaporization is introduced to the corona discharge area 19.

Since the first aperture electrode 11 is disposed at the position opposed to the APCI ion source 3, the introducing efficiency of the APCI ions to the first aperture electrode 11 can be enhanced.

Embodiment 2

The present embodiment is based on the device configuration described in Embodiment 1, and provides a voltage condition to improve the introducing efficiency of ESI ions to the first aperture electrode 11.

Figure 2:
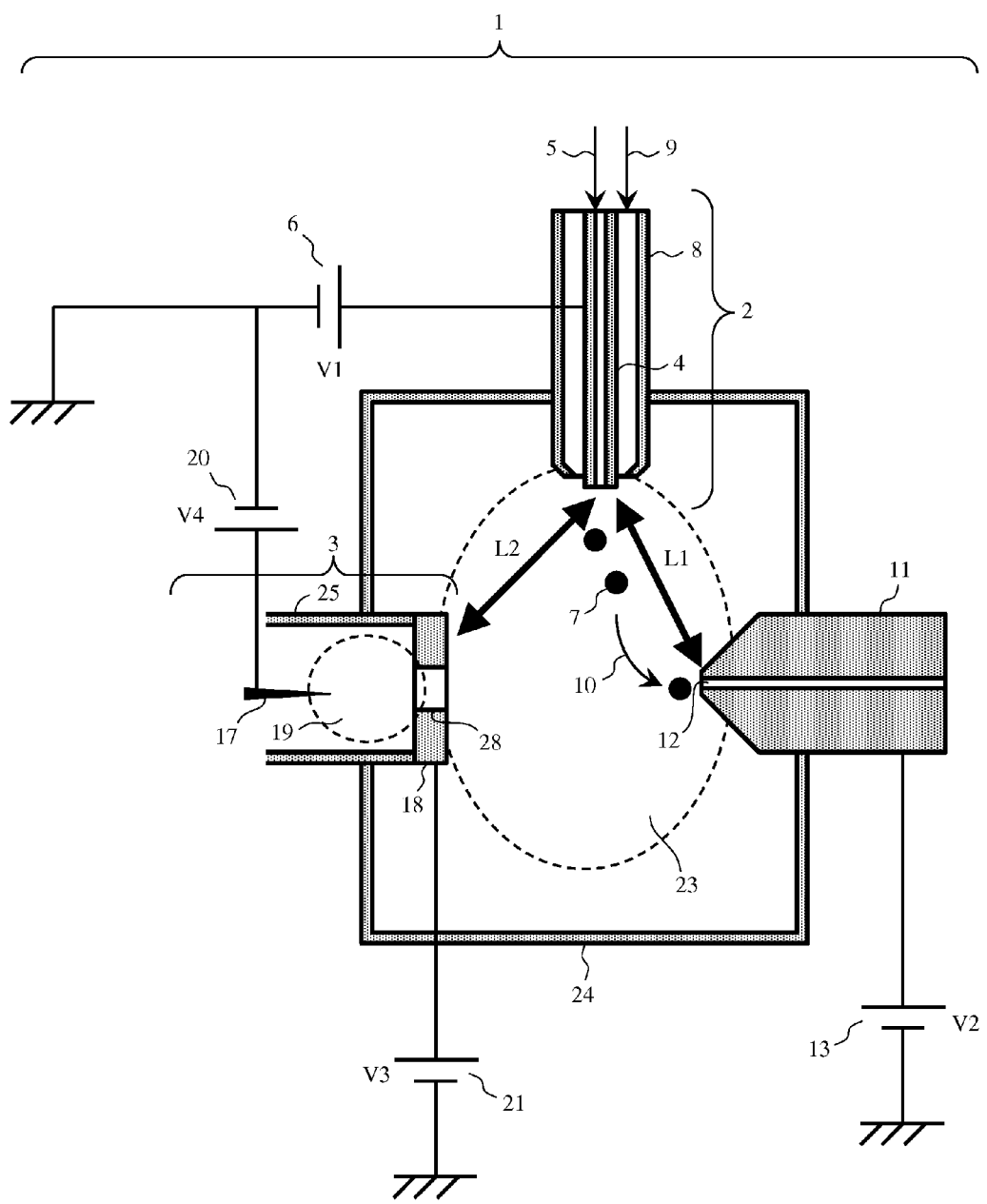
FIG. 2 describes voltage conditions to be used for a hybrid ion source according to Embodiment 2.

FIG. 2 schematically illustrates the configuration of a hybrid ion source 1 according to the present embodiment. In FIG. 2, the same reference numerals are assigned to elements corresponding to FIG. 1. The hybrid ion source 1 of the present embodiment has the same basic configuration as that of Embodiment 1. Note here that FIG. 2 omits the exhaust pump 27 or the like to be connected to the APCI ion source 3. The following describes differences from Embodiment 1 only.

In the following descriptions, V1 denotes a voltage value applied to the capillary 4 of the ESI ion source 2, V2 denotes a voltage value applied to the first aperture electrode 11, V3 denotes a voltage value applied to the counter electrode 18, and V4 denotes a voltage value applied to the needle electrode 17. L1 denotes the distance between the capillary 4 and the first aperture electrode 11, and L2 denotes the distance between the capillary 4 and the counter electrode 18.

Then estimates of the intensity of electric field (electrical intensity) E1 generated between the capillary 4 and the first aperture electrode 11 and of the intensity of electric field (electrical intensity) E2 generated between the capillary 4 and the counter electrode 18 can be calculated from Expression 1 and Expression 2, respectively:

$$E1 = |V1 - V2|/L1 \quad \text{(Ex. 1); and}$$

$$E2 = |V1 - V3|/L2 \quad \text{(Ex. 2).}$$

The present embodiment is configured so that electrical intensities E1 and E2 satisfy the relationship of Expression 3. That is, it is set so that electrical intensity E1 between the capillary 4 and the first aperture electrode 11 is larger than electrical intensity E2 between the capillary 4 and the counter electrode 18:

$$E1 > E2 \quad \text{(Ex. 3).}$$

Satisfying the condition of Expression 3 makes the ESI ions 7 generated by the ESI ion source 2 to travel easily along the orbit of the arrow 10, for example, in the direction to the first aperture electrode 11 having a larger electrical intensity. That is, they easily travel in the direction of the first aperture electrode 11 rather than in the direction of the counter electrode 18. This can increase the detected intensity of ESI ions.

The voltage value V3 applied to the counter electrode 18 of the APCI ion source 3 may be set at voltage so as to repel with electrical charge of the ESI ions 7. For instance, when the ESI ions 7 are positive ions, then a positive voltage value may be applied to the counter electrode 18, and when the ESI ions 7 are negative ions, then a negative voltage value may be applied to the counter electrode 18. In this case, a repelling force is generated between the ESI ions 7 and the counter electrode 18, so that the ESI ions 7 are easily deflected in the direction of the first aperture electrode 11. As a result, the introducing efficiency of the ESI ions 7 to the first aperture electrode 11 can be further improved.

As stated above, according to the present embodiment, the hybrid ion source having a substantially similar configuration to Embodiment 1 can have efficiently increased intensity of the ESI ions 7 generated there.

Embodiment 3

The present embodiment describes a hybrid ion source configured so that the ESI ion source 2 and the APCI ion source 3 are disposed at positions mutually opposed, and the APCI ion source 3 and the first aperture electrode 11 are disposed at mutually orthogonal positions. This embodiment aims to increase the air flow from the ESI ionization area 23 to the corona discharge area 19 and increase the intensity of APCI ions generated.

Figure 3:
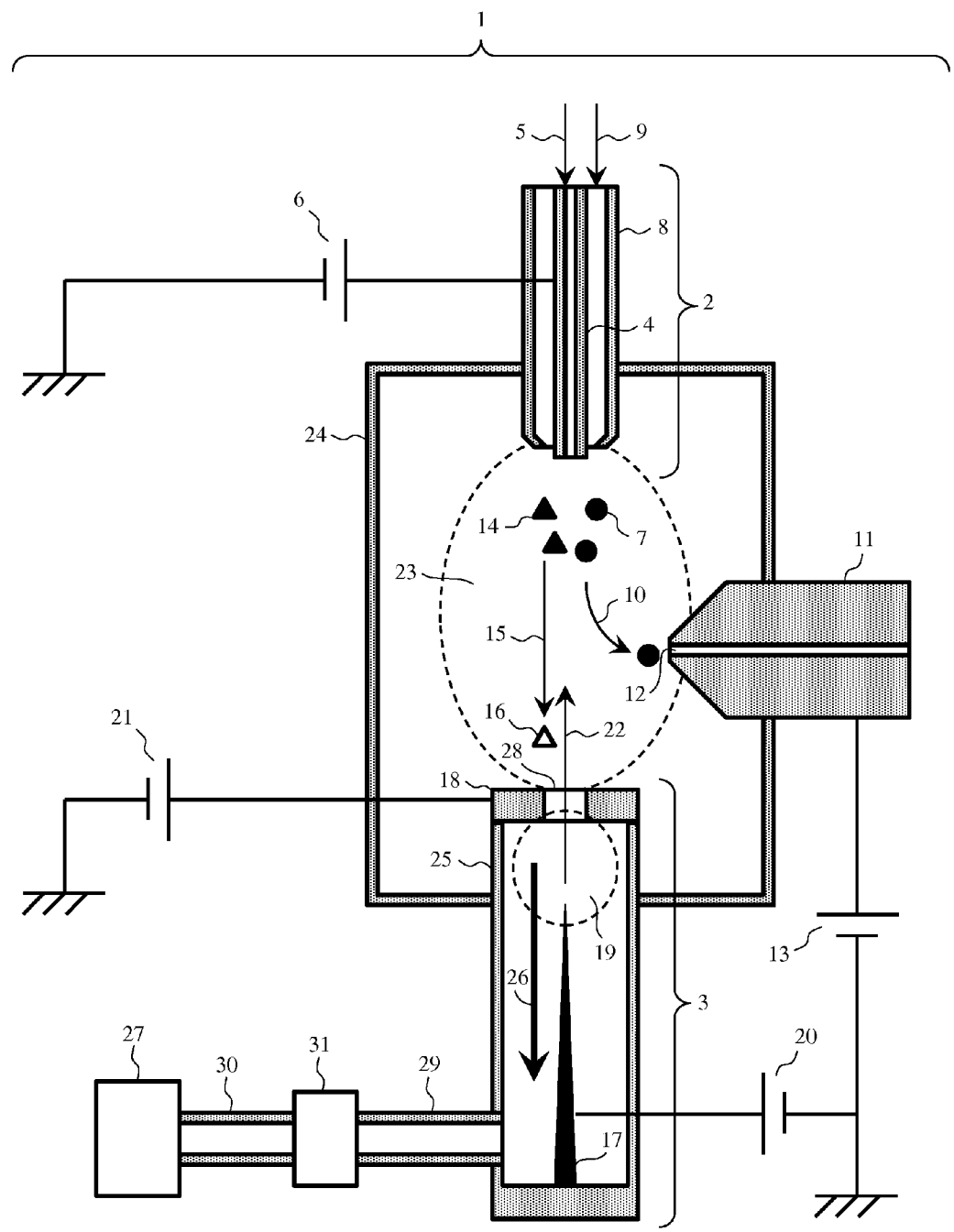
FIG. 3 illustrates a configuration of a hybrid ion source according to Embodiment 3.

FIG. 3 schematically illustrates the configuration of a hybrid ion source 1 according to the present embodiment. In FIG. 3, the same reference numerals are assigned to elements corresponding to FIG. 1. As illustrated in FIG. 3, the hybrid ion source 1 of the present embodiment has the same basic configuration as that of Embodiment 1. The following describes differences from Embodiment 1 only.

As illustrated in FIG. 3, the hybrid ion source 1 according to the present embodiment is configured so that the APCI ion source 3 is disposed substantially vertically below the ESI ion source 2. Similarly to FIG. 1, the first aperture electrode 11 is disposed to be extended horizontally. That is, the first aperture electrode 11 has a positional relationship orthogonal to both of the ESI ion source 2 and the APCI ion source 3.

The opening 12 at the forward end of the first aperture electrode 11 is disposed in an expected angle of a coneshaped ion orbit emitted from the opening of the APCI ion source 3 or in the range of the vicinity thereof.

In the case of the present embodiment, the direction of the gravity acting on the droplets 14 out of the sample solution 5 sprayed from the ESI ion source 2 that are not ionized agrees with the direction of the air flow. This can increase the introducing efficiency of the sample gas 16 to the corona discharge area 19 of the APCI ion source 3. As a result, the intensity of the APCI ions generated can be increased.

Note here that, in the case of the present embodiment, the output direction of the APCI ions and the opening 12 of the first aperture electrode 11 are not opposed, and so the arrangement and applied voltage are desirably optimized so as to introduce the APCI ions to the opening 12 effectively. For instance the APCI ion source 3 and the opening 12 are brought closer to each other.

In the present embodiment as well, voltage of each power source may be set so as to satisfy the electrical intensity conditions described in Embodiment 2, whereby the detected intensity of the ESI ions can be improved.

Embodiment 4

The present embodiment describes a hybrid ion source configured so that the ESI ion source, the APCI ion source and the first aperture electrode have a mutually orthogonal positional relationship.

Figure 4:
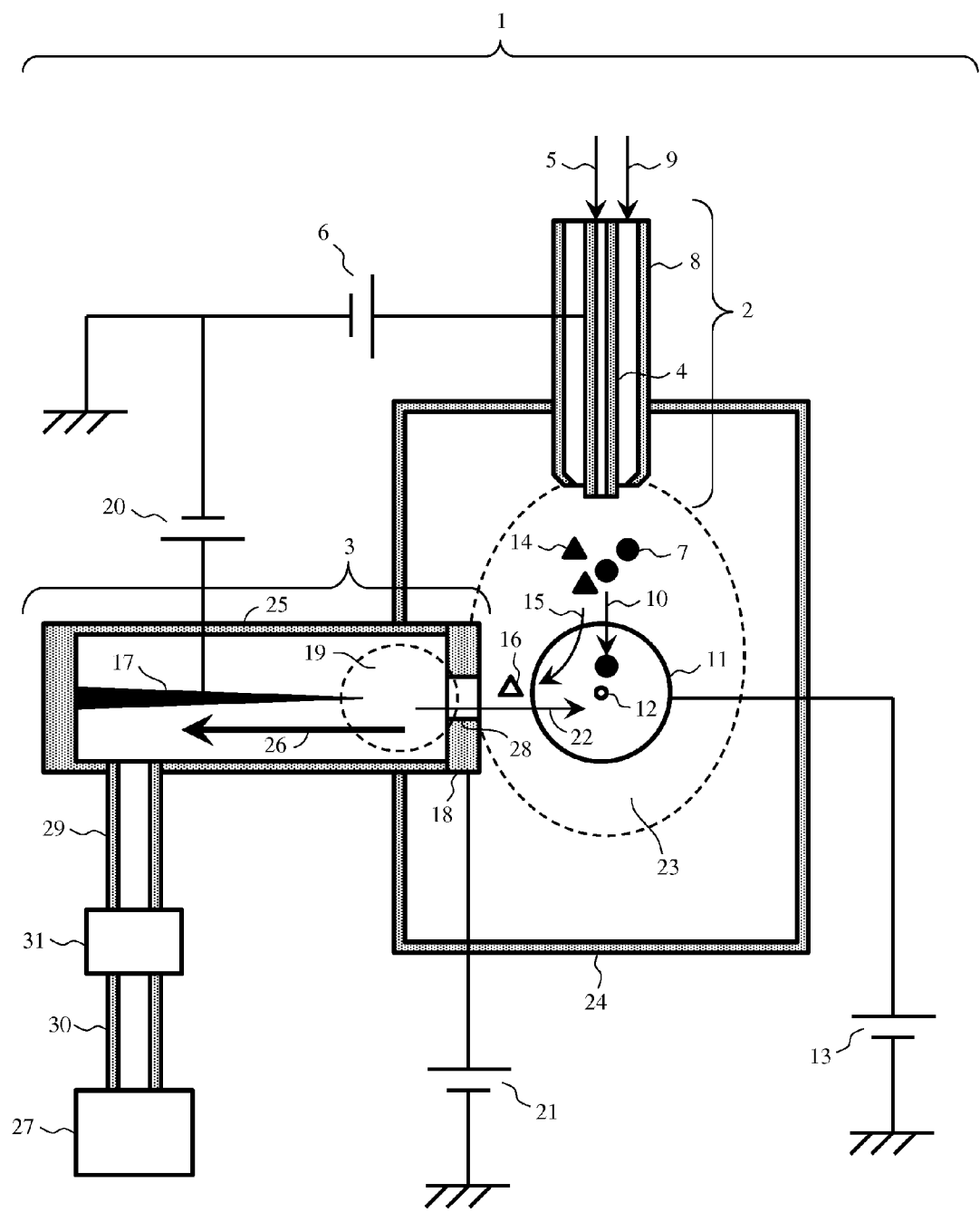
FIG. 4 illustrates a configuration of a hybrid ion source according to Embodiment 4.

FIG. 4 schematically illustrates the configuration of a hybrid ion source 1 according to the present embodiment. In FIG. 4, the same reference numerals are assigned to elements corresponding to FIG. 1. As illustrated in FIG. 4, the hybrid ion source 1 of the present embodiment has the same basic configuration as that of Embodiment 1. The following describes differences from Embodiment 1 only.

FIG. 4 is different in that the first aperture electrode 11 is attached in the direction perpendicular to the paper. In FIG. 4, the forward end part of the first aperture electrode 11 only is illustrated. This configuration can suppress the risk where a component of the droplets 14 that travels straight ahead because of insufficient vaporization is introduced to the corona discharge area 19. In this case as well, the sample gas 16 can be effectively introduced to the APCI ion source 3 along with the air flow, and so the intensity of the APCI ions generated can be improved. In the present embodiment as well, voltage of each power source may be set so as to satisfy the electrical intensity conditions described in Embodiment 2, whereby the detected intensity of the ESI ions can be improved.

Embodiment 5

The present embodiment describes a hybrid ion source configured so that the APCI ion source is attached to the side face of the ESI ionization chamber (chamber) from obliquely downward.

Figure 5:
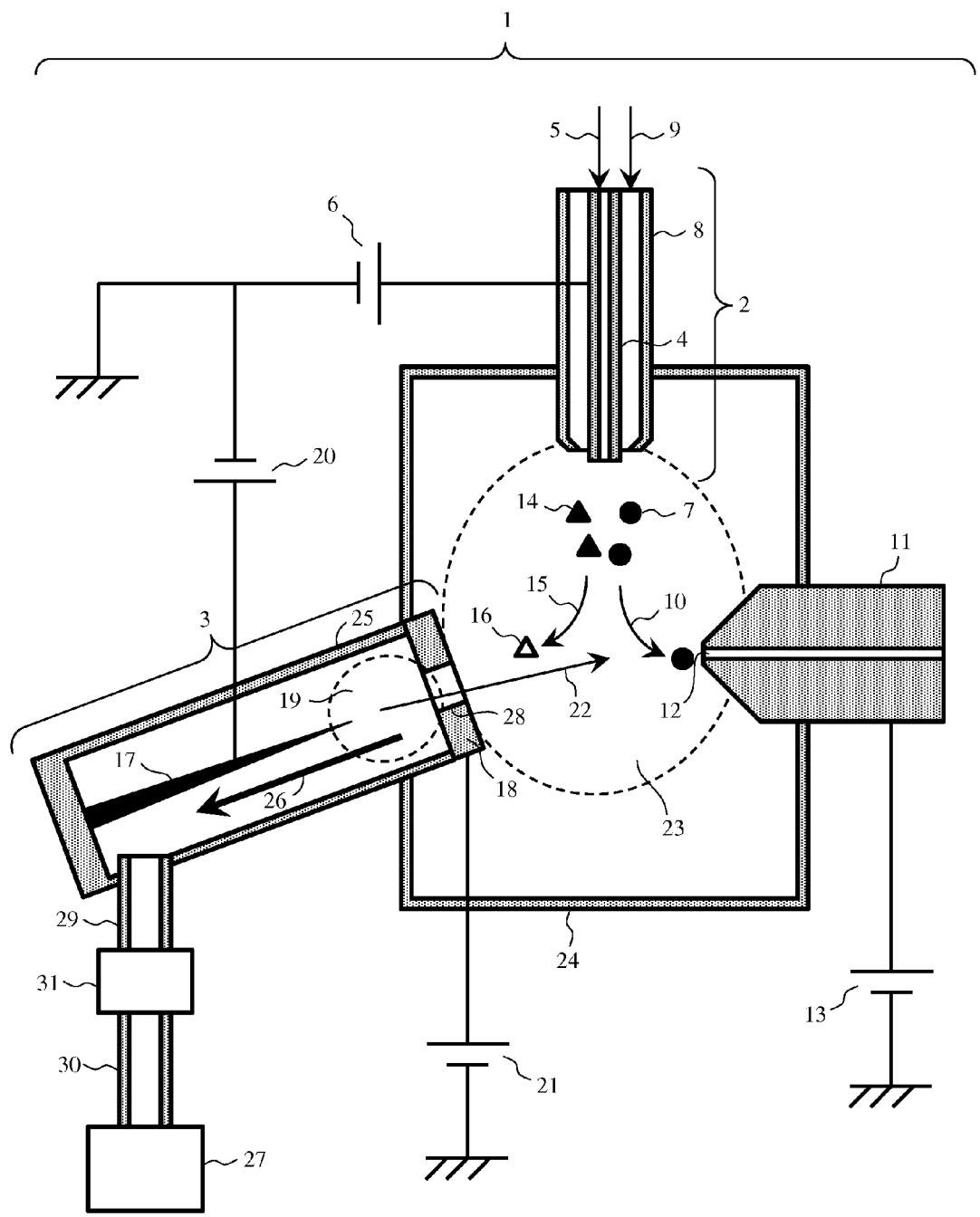
FIG. 5 illustrates a configuration of a hybrid ion source according to Embodiment 5.

FIG. 5 schematically illustrates the configuration of a hybrid ion source 1 according to the present embodiment. In FIG. 5, the same reference numerals are assigned to elements corresponding to FIG. 1. As illustrated in FIG. 5, the hybrid ion source 1 of the present embodiment has the same basic configuration as that of Embodiment 1. The following describes differences from Embodiment 1 only.

The APCI ion source 3 is attached to the side face of the chamber that is on the opposite side of the side face to which the first aperture electrode 11 is attached so that its axis line is inclined obliquely downward in the drawing. That is, the APCI ion source 3 is attached so that the front end direction of the needle electrode 17 is directed obliquely upward. The angle between the axis line direction of the APCI ion source 3 and the axis line direction of the ESI ion source 2 is an obtuse angle.

As described above, a part of the sample solution 5 sprayed from the ESI ion source 2 remains as droplets 14 due to insufficient vaporization. Then these droplets 14 mainly travel straight ahead. That is, as compared with the attachment configuration of Embodiment 3 (FIG. 3), this configuration can lower the risk where a component of the droplets 14 traveling straight ahead is introduced to the corona discharge area 19.

The sample gas 16 is generated through vaporization of the sample solution 5 sprayed vertically downward. When the introduction port of the APCI ion source 3 is attached obliquely upward, the sample gas 16 can be effectively introduced to the corona discharge area 19. Further the angle between the axis line direction of the APCI ion source 3 and the axis line direction of the first aperture electrode 11 is larger than that in Embodiment 3 (FIG. 3) (larger than 90°). This can increase the introducing efficiency of the APCI ions to the first aperture electrode 11 as compared with the case of Embodiment 3.

In this case as well, the similar effects to Embodiment 1 can be obtained basically. In the present embodiment as well, voltage of each power source may be set so as to satisfy the electrical intensity conditions described in Embodiment 2, whereby the detected intensity of the ESI ions can be improved.

Embodiment 6

The present embodiment describes a hybrid ion source having a substantially similar configuration to Embodiment 1, where heating mechanism is added to both of the enclosure of the APCI ion source and the needle electrode.

Figure 6:
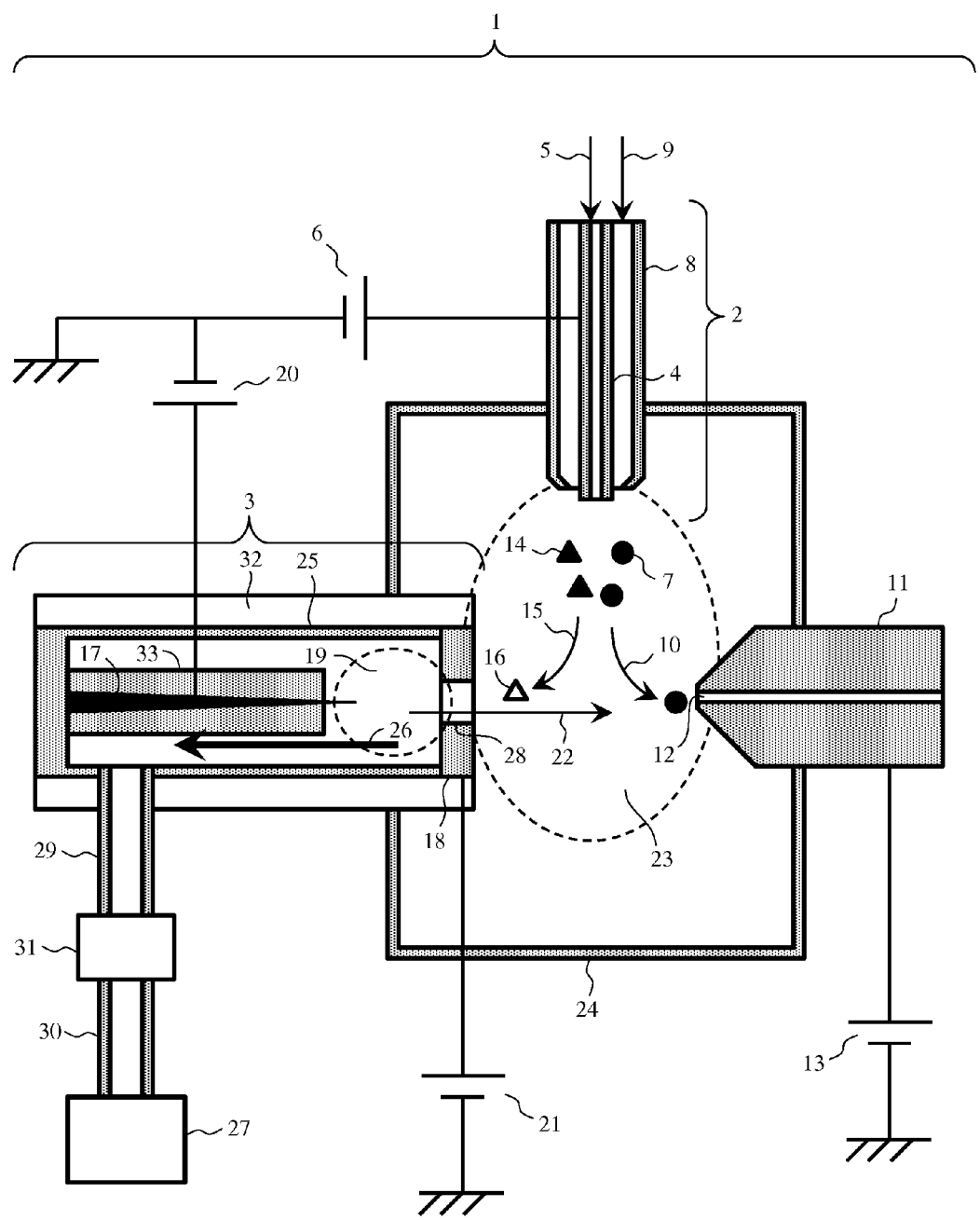
FIG. 6 illustrates a configuration of a hybrid ion source according to Embodiment 6.

FIG. 6 schematically illustrates the configuration of a hybrid ion source 1 according to the present embodiment. In FIG. 6, the same reference numerals are assigned to elements corresponding to FIG. 1. The hybrid ion source 1 of the present embodiment has the same basic configuration as that of Embodiment 1. The following describes differences from Embodiment 1 only.

In FIG. 6, a heating unit 32 to heat the enclosure of the APCI ion source 3 and a heating unit 33 to heat the needle electrode 17 are added.

The configuration of the present embodiment is especially effective for the case where a component having strong corrosive, such as acid, is mixed in the sample solution 5. The sample gas 16 vaporized from the sample solution 5 is introduced to the APCI ion source 3 along with the air flow 26, a part of which is attached to the inside of the enclosure or the surface of the needle electrode 17. Since the enclosure or the needle electrode 17 of the present embodiment is heated, the sample gas 16, even if it is attached there, is vaporized again, and is exhausted to the outside from the rear end side of the APCI ion source 3 along with the air flow. This can keep the inside of the enclosure of the APCI ion source 3 and the surface of the needle electrode 17 clean. As a result, the needle electrode 17 or the like can have longer life, and the durability and the stability thereof can be improved.

Although the present embodiment includes both of the heating units 32 and 33, it may include only one of the heating units. The heating units 32 and 33 may have various heating schemes, such as heating in a direct contact state with the enclosure or the needle electrode 17 as in a heat block or a heater wire, or heating in a non-contact state with the enclosure or the needle electrode 17 as in a lamp or infrared rays.

The present embodiment also can have the basic effects of Embodiment 1. The heating scheme of the present embodiment may be combined with the hybrid ion source 1 described in Embodiment 1 to 5 for use.

Embodiment 7

The present embodiment describes a hybrid ion source having a substantially similar configuration to Embodiment 1, where heating mechanism is added to heat the ESI ionization area.

Figure 7:
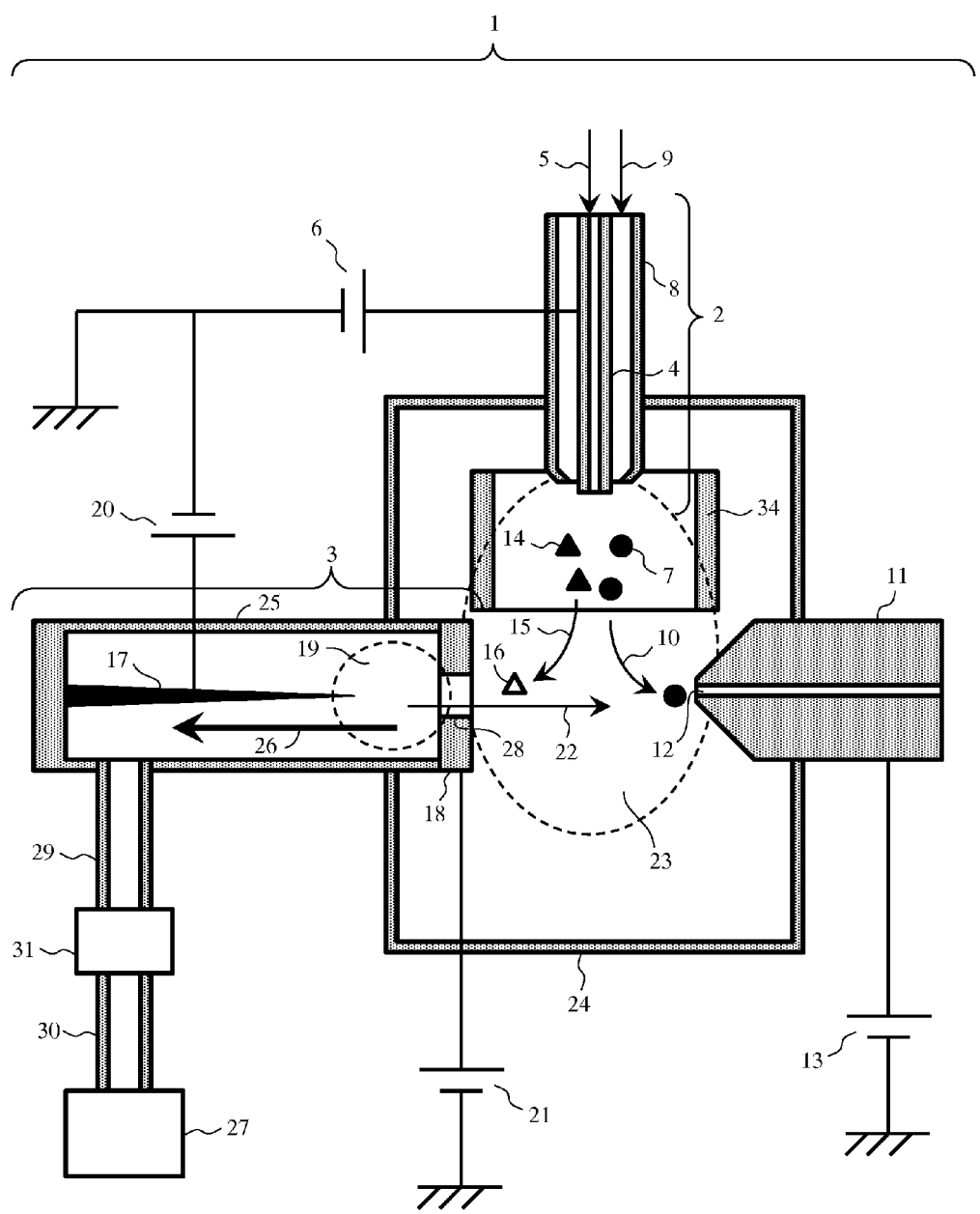
FIG. 7 illustrates a configuration of a hybrid ion source according to Embodiment 7.

FIG. 7 schematically illustrates the configuration of a hybrid ion source 1 according to the present embodiment. In FIG. 7, the same reference numerals are assigned to elements corresponding to FIG. 1. The hybrid ion source 1 of the present embodiment has the same basic configuration as that of Embodiment 1. The following describes differences from Embodiment 1 only.

In FIG. 7, a heating unit 34 to heat the ESI ionization area 23 is attached to the vicinity of the forward end of the ESI ion source 2. FIG. 7 especially illustrates an exemplary configuration to heat the vicinity of the exit of the capillary 4 mainly. The heating unit 34 of the present embodiment has a tubular shape.

In the case of the present embodiment, the heating unit 34 can heat the ESI ionization area 23, which promotes vaporization of the sample solution 5 and can improve the intensity of the ESI ions generated. Heating of the ESI ionization area 23 can promote vaporization of the droplets 14 as well. As a result, the generation efficiency of the sample gas 16 is improved, and the intensity of APCI ions generated also is improved.

The heating unit 34 may have various heating schemes, such as heating using a heat block, or heating using a lamp or infrared rays. The present embodiment also can have the basic effects of Embodiment 1. The heating scheme of the present embodiment may be combined with the hybrid ion source 1 described in Embodiments 1 to 6 for use.

Embodiment 8

The present embodiment describes a hybrid ion source having a substantially similar configuration to Embodiment 1, where heating mechanism is disposed at a position opposed to the ESI ion source.

Figure 8:
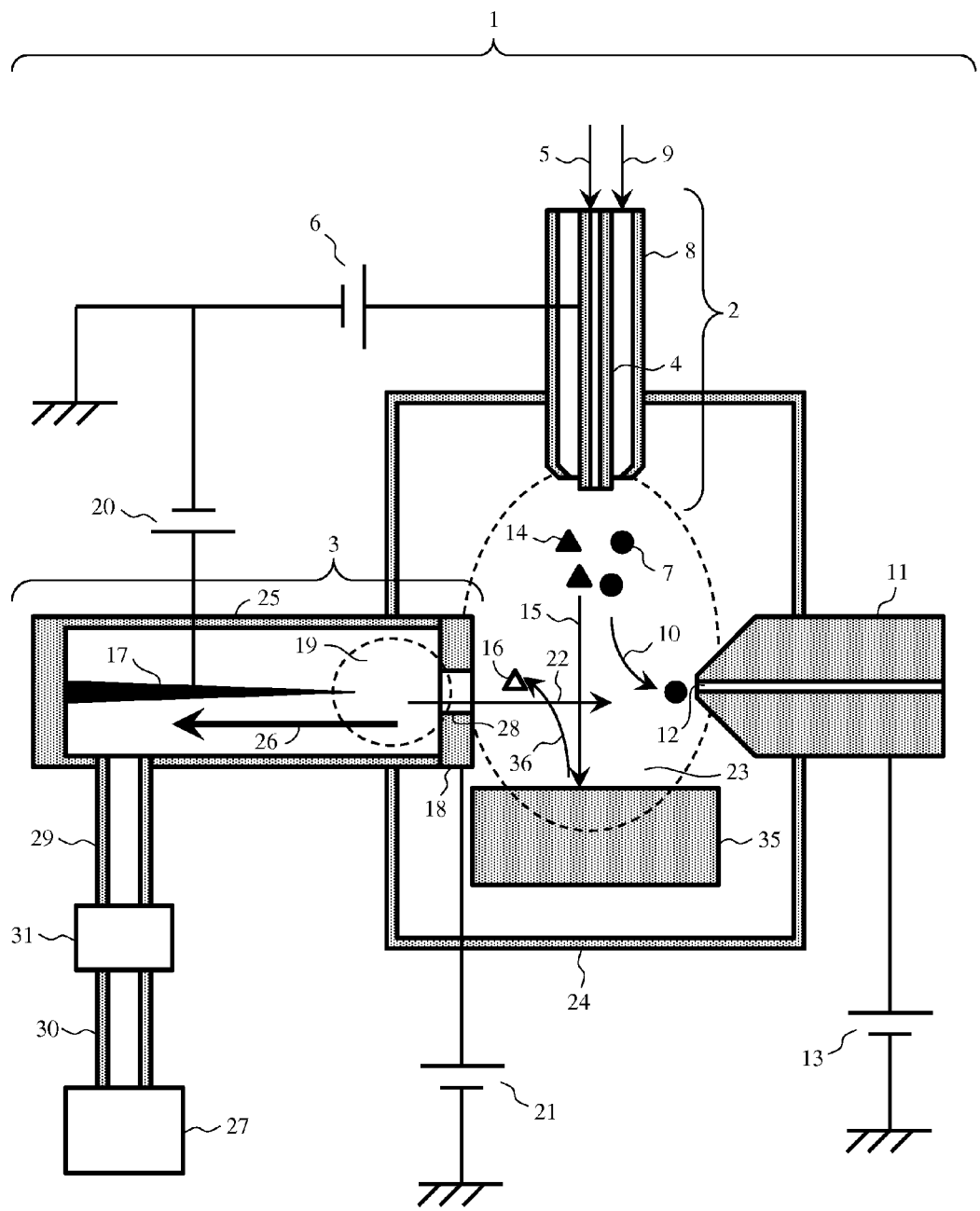
FIG. 8 illustrates a configuration of a hybrid ion source according to Embodiment 8.

FIG. 8 schematically illustrates the configuration of a hybrid ion source 1 according to the present embodiment. In FIG. 8, the same reference numerals are assigned to elements corresponding to FIG. 1. The hybrid ion source 1 of the present embodiment has the same basic configuration as that of Embodiment 1. The following describes differences from Embodiment 1 only.

In FIG. 8, a heating unit 35 to heat the ESI ionization area 23 is disposed just below the ESI ion source 2 and at a position lower than the attachment positions of the APCI ion source 3 and the first aperture electrode 11. The heating unit 35 includes a heating plate, for example. The heating unit 35 has a sufficient area for an expected range where the droplets 14 are expanded or an expected range where the ESI ionization area 23 are expanded.

With such arrangement and configuration, the ESI ionization area 23 is entirely heated from the below to promote the vaporization of the sample solution 5, whereby intensity of the ESI ions generated can be improved. Vaporization of the droplets 14 also is promoted, and so the generation of the sample gas 16 can be promoted.

A part of the droplets 14 or the like sprayed from the capillary 4 passes along the orbit of arrow 15, for example, and directly collides with the heating unit 35. Such collision breaks up the droplets 14 or the like into smaller pieces, which are then effectively heated by the heating unit 35, meaning that vaporization can be further promoted. As a result, the amount of the sample gas 16 generated in the ESI ionization chamber 24 can be increased.

The sample gas 16 generated flows along the air flow formed in the ESI ionization chamber 24 (e.g., passing along the orbit of arrow 36), and is introduced to the APCI ion source 3. In this way, the present embodiment can promote ionization of the sample solution 5 and gasification of the droplets 14. Droplets colliding with the heating unit 35 while keeping the state of the droplets 14 also can be gasified, and so the intensity of APCI ions generated can be increased.

Gasification of the droplets 14 can reduce contamination in the ESI ionization chamber 24 due to the droplets 14 attached, and so influences on the mass spectrometry or the like can be reduced.

The heating unit 35 may have various heating schemes, such as heating using a heat block, or heating using a lamp or infrared rays. The present embodiment also can have the basic effects of Embodiment 1. The heating scheme of the present embodiment may be combined with the hybrid ion source 1 described in Embodiments 1 to 7 for use.

Embodiment 9

The present embodiment describes a hybrid ion source having a substantially similar configuration to Embodiment 1, where a heating gas pipe is disposed so as to introduce heating gas to the ESI ionization area and promote ionization and gasification.

Figure 9:
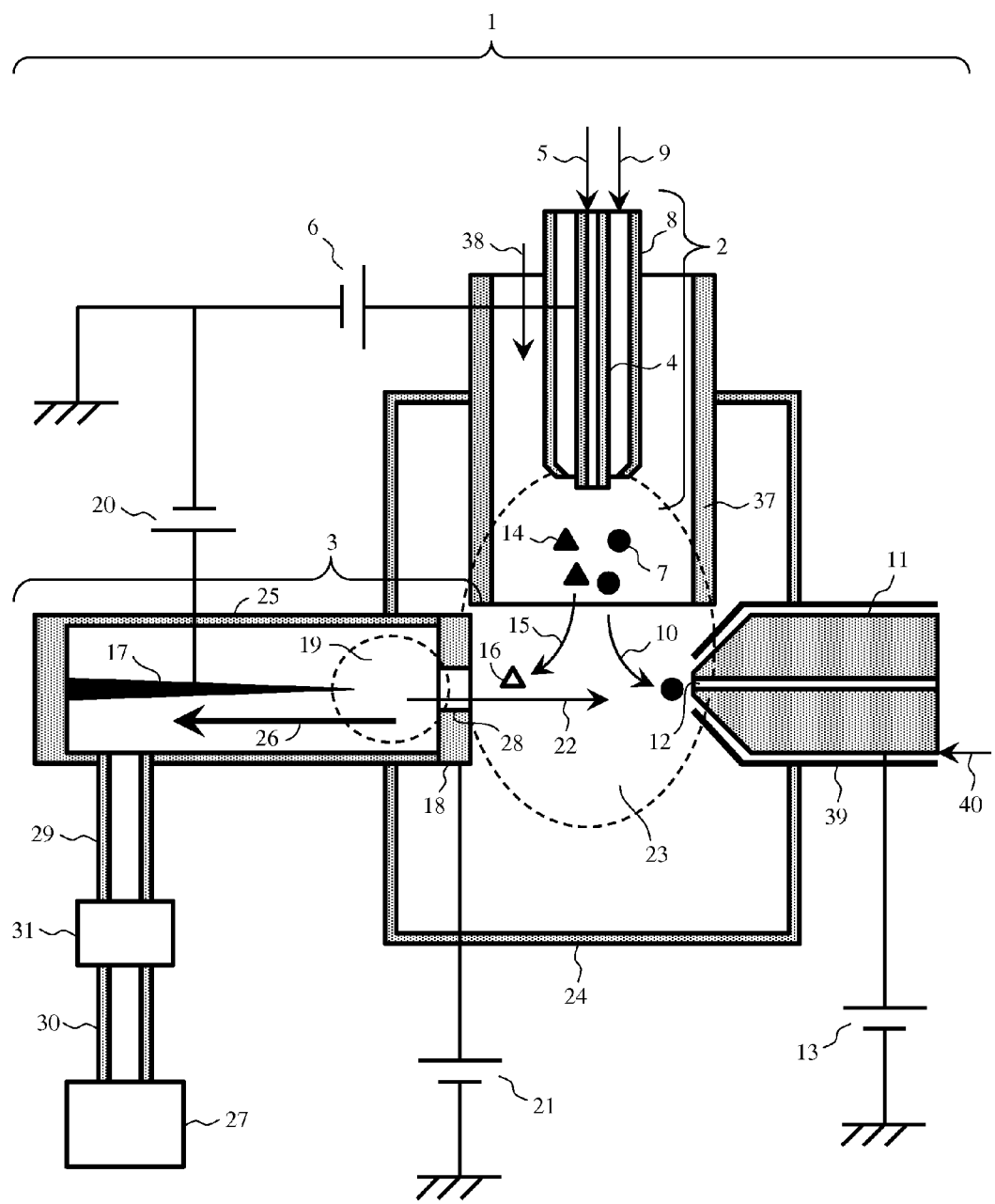
FIG. 9 illustrates a configuration of a hybrid ion source according to Embodiment 9.

FIG. 9 schematically illustrates the configuration of a hybrid ion source 1 according to the present embodiment. In FIG. 9, the same reference numerals are assigned to elements corresponding to FIG. 1. The hybrid ion source 1 of the present embodiment has the same basic configuration as that of Embodiment 1. The following describes differences from Embodiment 1 only.

In FIG. 9, a heating gas pipe 37 to heat the ESI ionization area 23 is disposed so as to surround the circumference of the ESI ion source 2. As in FIG. 9, a part of the ESI ionization area 23 may be present between the heating gas pipe 37 and the forward end of the capillary 4 in some cases. Heating gas 38 that is introduced from a heating gas source, not illustrated, flows through the heating gas pipe 37.

Since the ESI ionization area 23 is heated by the heating gas 38, vaporization of the sample solution 5 sprayed from the capillary 4 is further promoted, and so the intensity of the ESI ions generated is improved. The promotion of vaporization leads to improvement in generation efficiency of the sample gas 16 as well. This can improve the intensity of the APCI ions generated as well.

The heating gas 38 typically used is inert gas, such as nitrogen, and temperature thereof is up to about 800° C. by heating. The heating gas 38 may have the flow rate up to about a few tens of L/min for use.

In the present embodiment, an electrode 39 is disposed on the outside of the first aperture electrode 11, and gas 40 is allowed to flow through a gap between the electrode 39 and the first aperture electrode 11. The gas 40 is blown out from the vicinity of the inlet of the first aperture electrode 11, and generates air flow in the direction opposite of the ion introduction direction. Such air flow prevents substances other than ions from being introduced to the first aperture electrode 11. That is, this can reduce noise.

The gas 40 typically used also is inert gas, such as nitrogen. The gas 40 may have the flow rate up to about a few L/min for use. Only one of the heating gas 38 and the gas 40 may be used.

Voltage up to about 1 kV (absolute value) is typically applied to the electrode 39. In order to generate positive ions as the ESI ions, positive voltage is applied to the electrode 39, and in order to generate negative ions as the ESI ions, negative voltage is applied to the electrode 39.

The present embodiment also can have the basic effects of Embodiment 1. The heating scheme of the present embodiment may be combined with the hybrid ion source 1 described in Embodiments 1 to 8 for use.

Embodiment 10

The present embodiment describes a hybrid ion source having a substantially similar configuration to Embodiment 9, where an exhaust pump is disposed for direct exhaust of the ESI ionization chamber.

Figure 10:
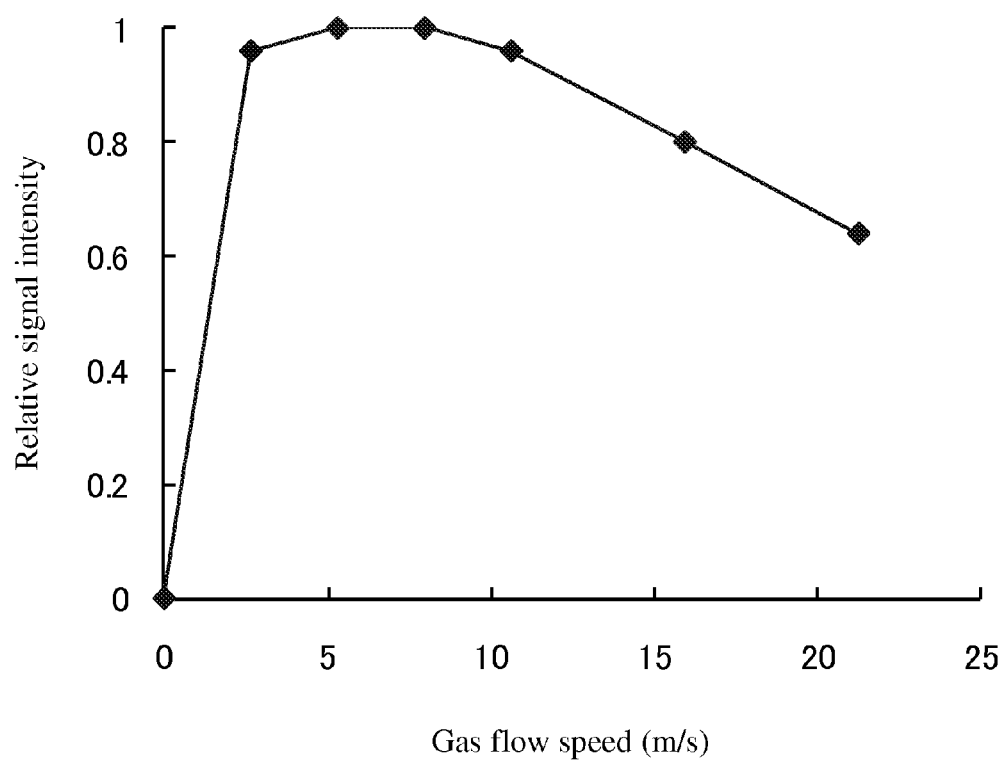
FIG. 10 describes the relationship between gas flow speed and ion generation intensity in the APCI ion source of the hybrid ion source according to Embodiments 1 to 9.

Firstly FIG. 10 illustrates the result of APCI ionization of heptachlorodibenzo-p-dioxin (HpCDD) using the hybrid ion sources 1 described in Embodiments 1 to 9. In FIG. 10, the horizontal axis represents gas flow speed, and the vertical axis represents relative signal intensity. FIG. 10 illustrates a change in intensity of the HpCDD ions (m/z406) when the gas flow speed in the vicinity of the opening 28 of the counter electrode 18 is changed by the air flow 26 in the APCI ion source 3. It can be found from FIG. 10 that the optimum condition for gas flow speed is about 2 to 10 m/s.

Meanwhile various gases are typically introduced as stated above, whose flow rate reaches up to a few tens of L/min, to the ESI ion source 2, so as to improve the ion intensity. As described above, the hybrid ion sources 1 according to Embodiments 1 to 9 include an exhaust port at a deep position of the APCI ion source 3, to which the exhaust pump 27 is connected. With this configuration, when the ESI ionization chamber 24 has a configuration close to hermetically sealing, the entire gas introduced to the ESI ionization chamber 24 will flow toward the APCI ion source 3 because of influences from the air flow 26 formed by the exhaust pump 27.

FIG. 10 illustrates the result obtained when the opening 28 of the counter electrode 18 is 2 mm in diameter. In the case of FIG. 10, the optimum value converted into the flow rate is about 0.5 to 2 L/min, which is different from the maximum gas flow rate (a few tens of L/min) of the ESI ion source 2 by one digit or more. That is, if the gas flow rate at the ESI ion source 2 is directly applied to the APCI ion source 3, the intensity of the APCI ions generated will be lowered.

Figure 11:
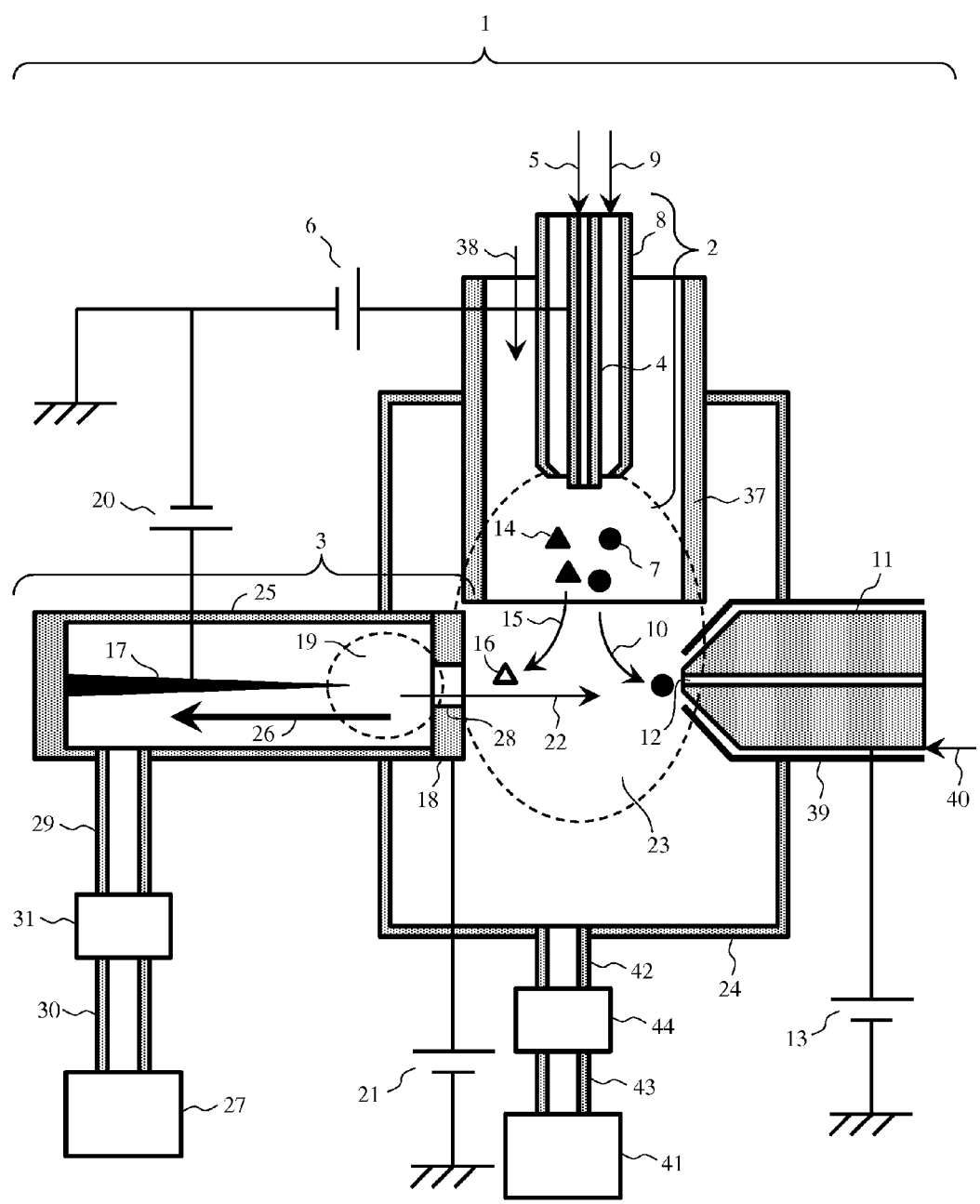
FIG. 11 illustrates a configuration of a hybrid ion source according to Embodiment 10.

To solve this problem, the present embodiment provides a hybrid ion source 1 having a configuration as illustrated in FIG. 11.

The basic configuration of FIG. 11 is similar to that of FIG. 9. Then in FIG. 11, the same reference numerals are assigned to elements corresponding to FIG. 9. The following are descriptions on Embodiment 10 about differences from Embodiment 9 only. The new configuration in the present embodiment includes an exhaust pump 41 for direct exhaust of the ESI ionization chamber 24.

The capacity of the exhaust pump 41 is up to about a few tens of L/min. The flow rate of gas exhausted from the ESI ionization chamber 24 is adjusted by a flow-rate adjustment mechanism 44 disposed at some part along the pipes 42 and 43 connecting the ESI ionization chamber 24 and the exhaust pump 41. The flow-rate adjustment mechanism 44 may include a flow controller, a valve or the like. When the exhaust pump 41 has a flow-rate adjustment function, or when the capacity of the exhaust pump 41 is the optimum flow rate, the flow-rate adjustment mechanism 44 is not essential.

In the case of the present embodiment, exhaust in the ESI ionization chamber 24 by the exhaust pump 41 can prevent the flow of gas of excessive amount to the APCI ion source 3, and can keep the flow speed of gas flowing into the APCI ion source 3 at the optimum value.

As a result, the hybrid ion source of the present embodiment can achieve both of the intensity of ESI ions generated and the intensity of APCI ions generated, as well as the basic effects of Embodiment 9. The present embodiment may be combined with the hybrid ion source 1 described in Embodiments 1 to 8 for use.

Embodiment 11

The present embodiment describes a hybrid ion source having a substantially similar configuration to Embodiment 9, where the diameter of the opening of the counter electrode is optimized so that the flow speed condition of sample gas introduced to the APCI ion source can be optimized.

The basic configuration of the hybrid ion source 1 in the present embodiment is similar to that of FIG. 9. The following describes differences from Embodiment 9 only, with reference to FIG. 9.

Similarly to Embodiment 10, the present embodiment also aims to keep the optimum flow speed condition described in FIG. 10. In the present embodiment, however, the opening 28 of the counter electrode 18 has a relatively large diameter.

The following describes the exemplary case based on the optimum flow rate condition (about 0.5 to 2 L/min) obtained by conversion of the result of FIG. 10, where the total flow rate of various gases introduced to the ESI ion source 2 is 10 times the optimum flow rate.

Since FIG. 10 illustrates the result when the opening 28 of the counter electrode 18 has a diameter of 2 mm, then in order to realize the same flow speed condition for 10 times the gas flow rate, it can be found that the opening 28 of the counter electrode 18 may have a diameter of about 6.3 mm based on the relationship of flow speed=flow rate/sectional area.

The present embodiment describes only one example, and the optimum diameter of the opening 28 of the counter electrode 18 depends on the total flow rate of various gases introduced to the ESI ion source 2.

The diameter of the opening 28 formed at the counter electrode 18 optimized as in the present embodiment can achieve both of the intensity of ESI ions generated and the intensity of APCI ions generated, as well as the basic effects of Embodiment 9. The counter electrode 18 of the present embodiment may be combined with the hybrid ion source 1 described in Embodiments 1 to 8 or 10 for use.

Embodiment 12

The present embodiment describes a hybrid ion source having a substantially similar configuration to Embodiment 9, where the flow speed condition of sample gas to be introduced to the APCI ion source is optimized by increasing the number of openings of the counter electrode.

Figure 12:
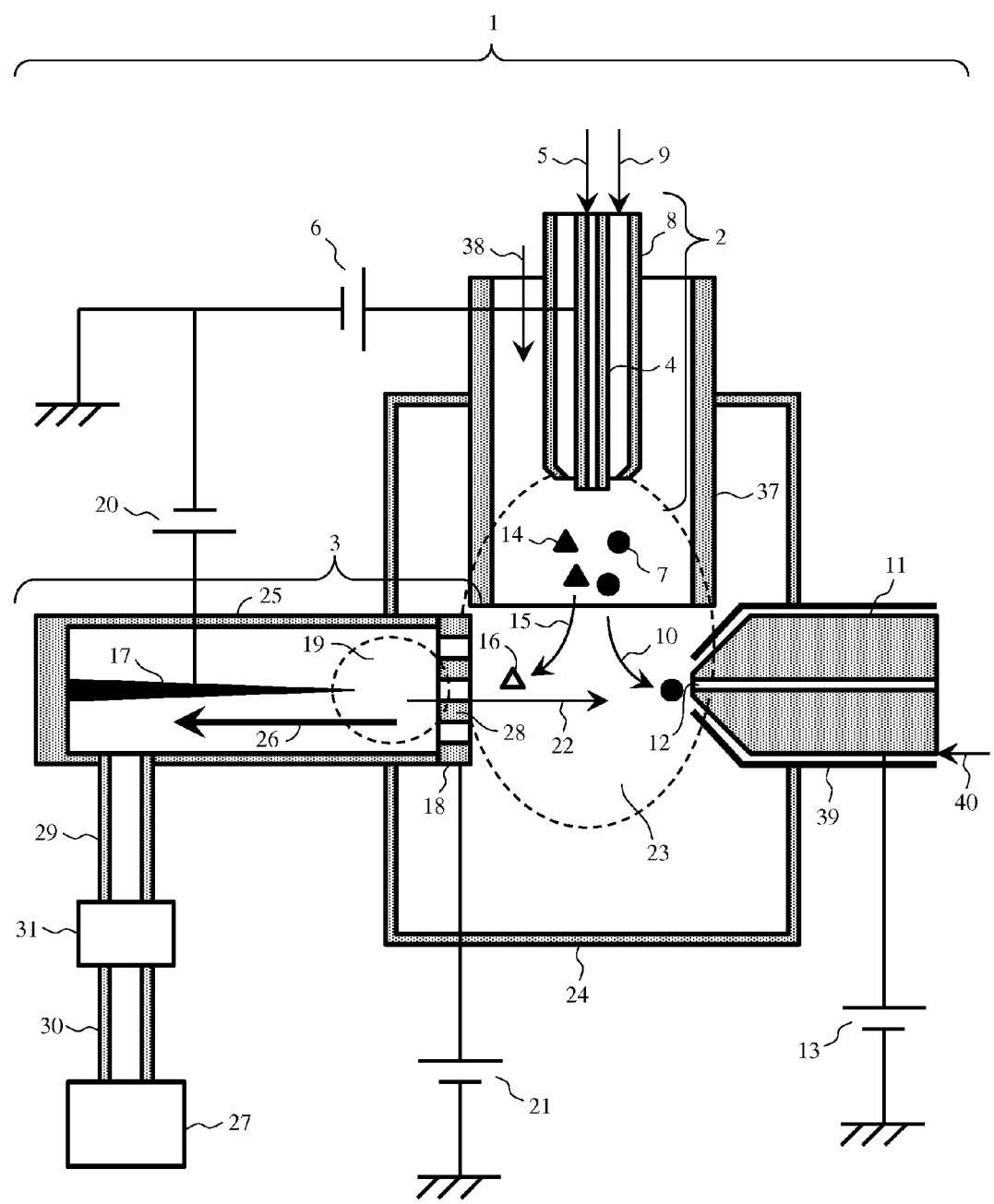
FIG. 12 illustrates a configuration of a hybrid ion source according to Embodiment 12.

FIG. 12 schematically illustrates the configuration of a hybrid ion source 1 according to the present embodiment. The basic configuration of the hybrid ion source 1 in the present embodiment is similar to that of FIG. 9. In FIG. 12, the same reference numerals are assigned to elements corresponding to FIG. 9. The following describes differences from Embodiment 9 only.

Figure 13A:
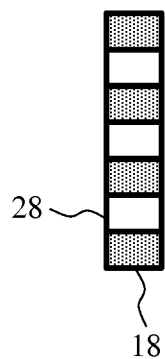
FIG. 13A describes a cross-sectional structure at the center of a counter electrode in Embodiment 12.
Figure 13B:
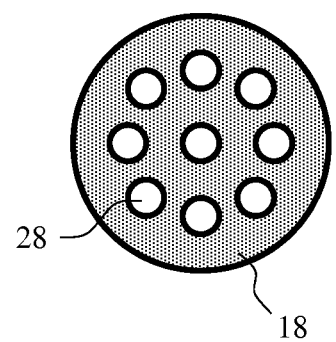
FIG. 13B describes a front-face structure of the counter electrode in Embodiment 12.

Similarly to Embodiment 10 as stated above, the present embodiment also aims to keep the optimum flow speed condition described in FIG. 10. In the present embodiment, however, the counter electrode 18 used includes a plurality of openings 28 as illustrated in FIGS. 13A and 13B.

In the case of the present embodiment, the disk-shaped counter electrode 18 has one opening 28 located at the center and eight openings 28 disposed on the same radius at regular intervals. In the present embodiment, the openings 28 have the same diameter.

The most important thing is not the number, the diameter and the arrangement of the openings 28 but the total cross-sectional area of the openings 28 formed at the counter electrode 18. That is, the total cross-sectional area at the counter electrode 18 is set so as to keep the optimum flow speed condition to the APCI ion source 3. The plurality of openings 28 at the counter electrode 18 may have different diameters, for example, as long as the total cross sectional area satisfies the flow speed condition.

The hybrid ion source of the present embodiment can achieve both of the intensity of ESI ions generated and the intensity of APCI ions generated, as well as the basic effects of Embodiment 9. The counter electrode 18 of the present embodiment may be combined with the hybrid ion source 1 described in Embodiments 1 to 8, 10, or 11 for use.

Embodiment 13

The present embodiment describes a hybrid ion source having a substantially similar configuration to Embodiment 9, where the counter electrode has a mesh structure where a plurality of openings are disposed like a net so as to optimize the flow speed condition of sample gas to be introduced to the APCI ion source.

Figure 14:
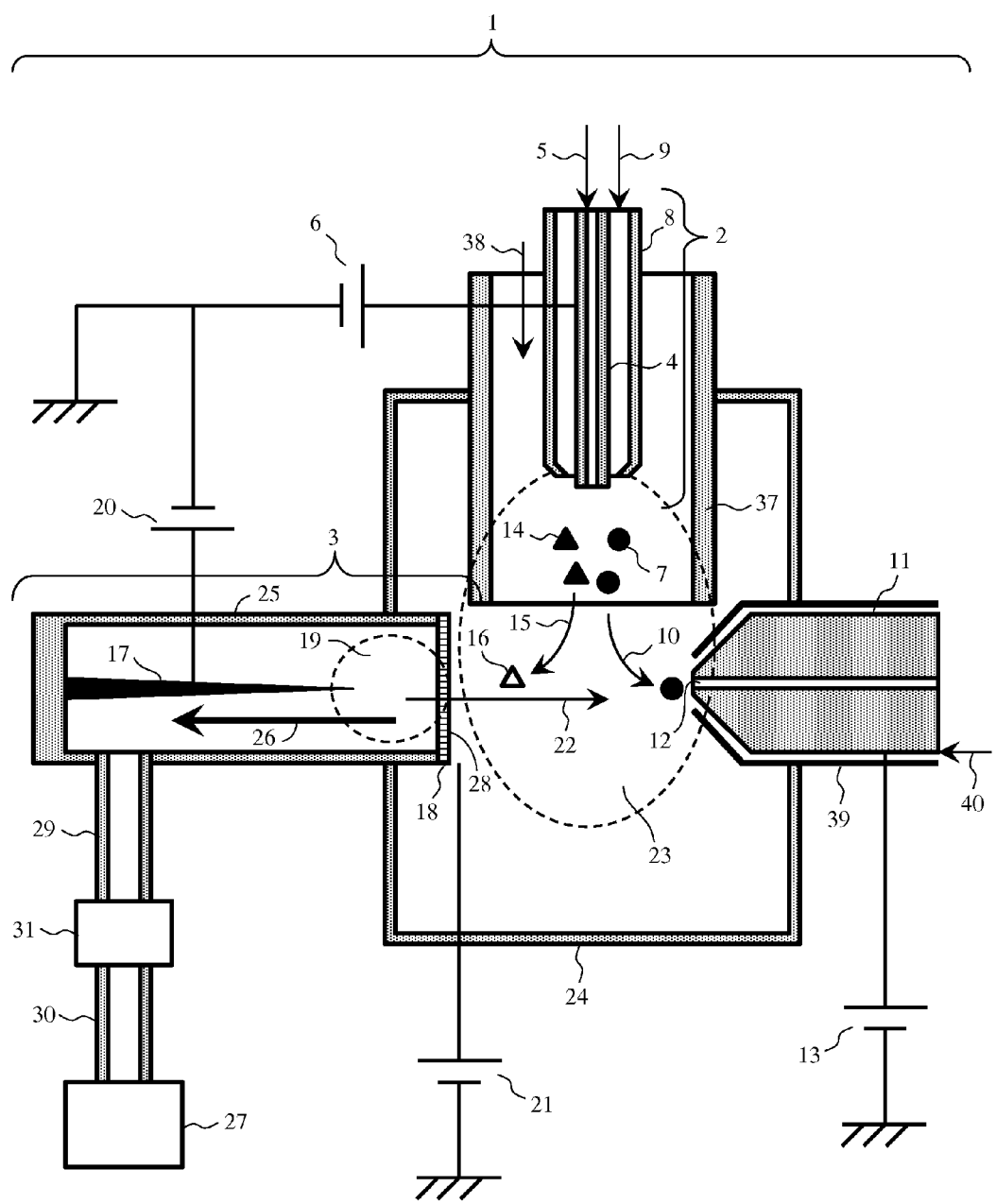
FIG. 14 illustrates a configuration of a hybrid ion source according to Embodiment 13.

FIG. 14 schematically illustrates the configuration of a hybrid ion source 1 according to the present embodiment. The basic configuration of the hybrid ion source 1 in the present embodiment is similar to that of FIG. 9. In FIG. 14, the same reference numerals are assigned to elements corresponding to FIG. 9. The following describes differences from Embodiment 9 only.

Figure 15A:
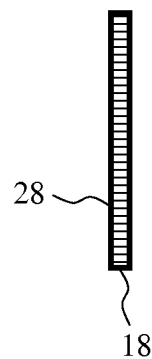
FIG. 15A describes a cross-sectional structure at the center of a counter electrode in Embodiment 13.
Figure 15B:
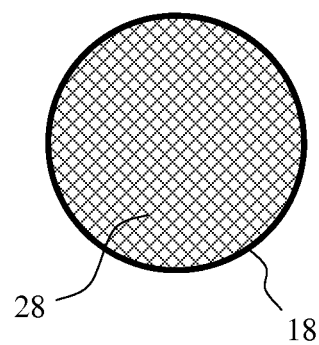
FIG. 15B describes a front-face structure of the counter electrode in Embodiment 13.

Similarly to Embodiment 10 as stated above, the present embodiment also aims to keep the optimum flow speed condition described in FIG. 10. In the present embodiment, however, the counter electrode 18 used has a mesh structure where a plurality of openings are disposed like a net as illustrated in FIGS. 15A and 15B. In the case of the present embodiment, the almost entire face of the counter electrode 18 is used as the opening. The total cross-sectional area of the openings 28 formed depends on the thickness of the wires making up the counter electrode 18. Typically a thicker wire diameter means a smaller cross-sectional area.

The total cross-sectional area at the counter electrode 18 is set so as to keep the optimum flow speed condition to the APCI ion source 3. The hybrid ion source of the present embodiment can achieve both of the intensity of ESI ions generated and the intensity of APCI ions generated, as well as the basic effects of Embodiment 9. The counter electrode 18 of the present embodiment may be combined with the hybrid ion source 1 described in Embodiments 1 to 8, 10, or 11 for use.

Embodiment 14

The present embodiment describes a hybrid ion source according to Embodiment 1, where a plurality of APCI ion sources 3 are disposed.

Figure 16:
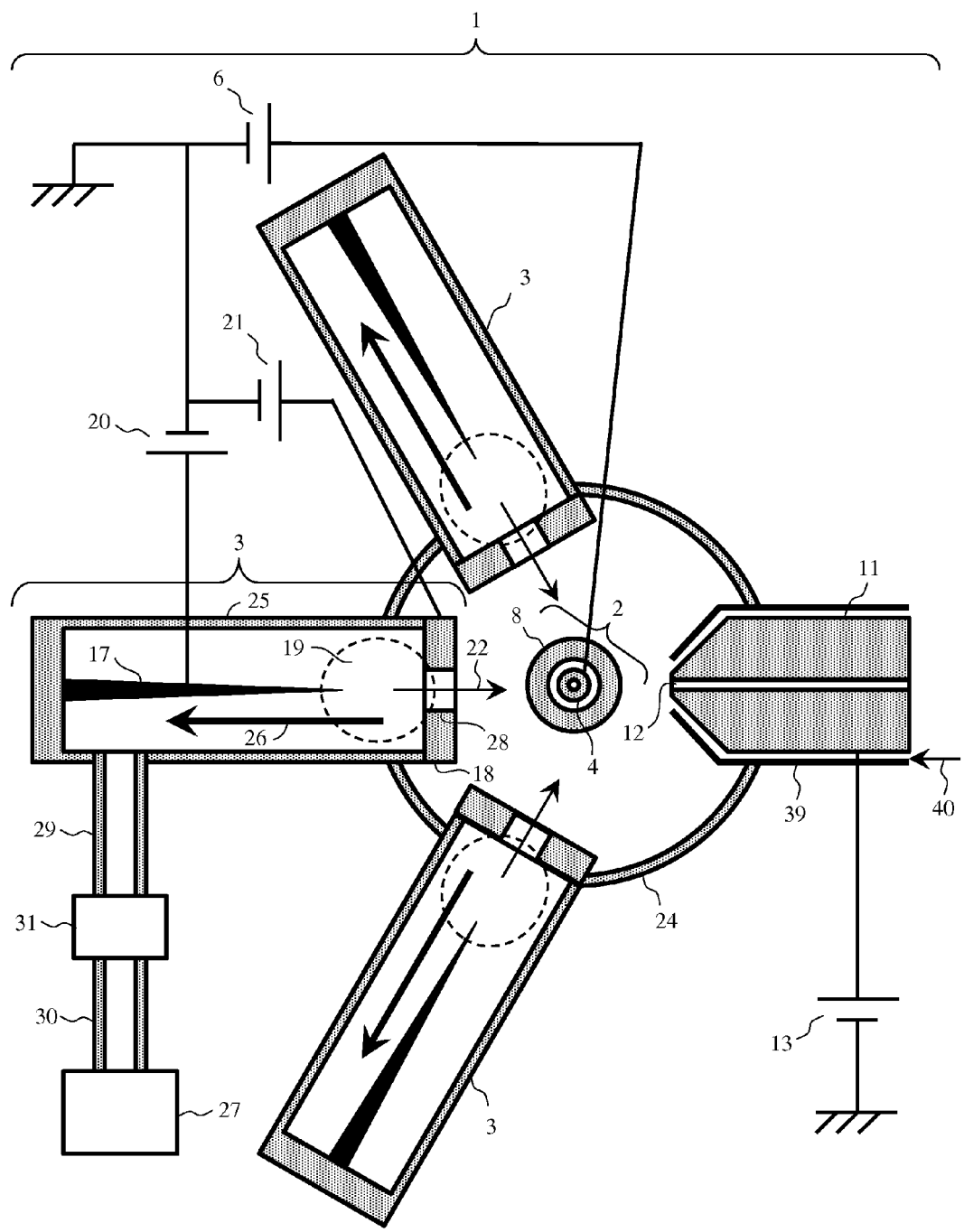
FIG. 16 illustrates a configuration of a hybrid ion source according to Embodiment 14.

FIG. 16 schematically illustrates the configuration of a hybrid ion source 1 according to the present embodiment. In FIG. 16, the same reference numerals are assigned to elements corresponding to FIG. 9. Note here that FIG. 16 illustrates the cross-sectional configuration of the hybrid ion source 1 upwardly viewed from the bottom-face side facing the ESI ion source 2. The heating gas pipe 37 is not illustrated in this drawing.

Since FIG. 16 is a cross-sectional view that is upwardly viewed from the bottom-face side facing the ESI ion source 2, the forward ends of the capillary 4 and the spray pipe 8 are represented concentrically. The cross-sectional shape of the ESI ionization chamber 24 also is represented concentrically with the capillary 4.

In the case of FIG. 16, three APCI ion sources 3 are disposed along the circumference of the ESI ionization chamber 24. FIG. 16 illustrates only one of the APCI ion sources 3 that is connected to the exhaust pump 27 via pipes 29 and 30, and the two other APCI ion sources 3 also have the same configuration.

The present embodiment includes a plurality of APCI ion sources 3 attached to the ESI ionization chamber 24, and so the amount (flow speed) of the sample gas 16 introduced to each APCI ion source 3 can be reduced as compared with Embodiment 9. As a result, the flow speed condition of the sample gas 16 at each APCI ion source 3 can be kept at the optimum condition.

Further, the intensity of APCI ions generated at each APCI ion source 3 also can be increased, and so more APCI ions can be supplied to the ESI ionization chamber 24 than in other embodiments.

Although there is a restriction for attachment, each APCI ion source 3 is disposed so that the ion introduction port of the first aperture electrode 11 is located in an expected angle of a cone-shaped ion orbit emitted from the opening of the APCI ion source or in the range of the vicinity thereof.

The hybrid ion source of the present embodiment can achieve both of the intensity of ESI ions generated and the intensity of APCI ions generated, as well as the basic effects of Embodiment 9. The counter electrode 18 of the present embodiment may be combined with the hybrid ion source 1 described in Embodiments 1 to 8 or 10 to 13 for use.

Embodiment 15

The present embodiment describes a hybrid ion source having a substantially similar configuration to Embodiment 1, where a power source applying voltage to each electrode used is capable of switching the voltage applied rapidly, and the hybrid ion source has an additional function of changing the exhaust flow rate from the ESI ionization area to the corona discharge area in response to the switching timing of the power source.

Figure 17:
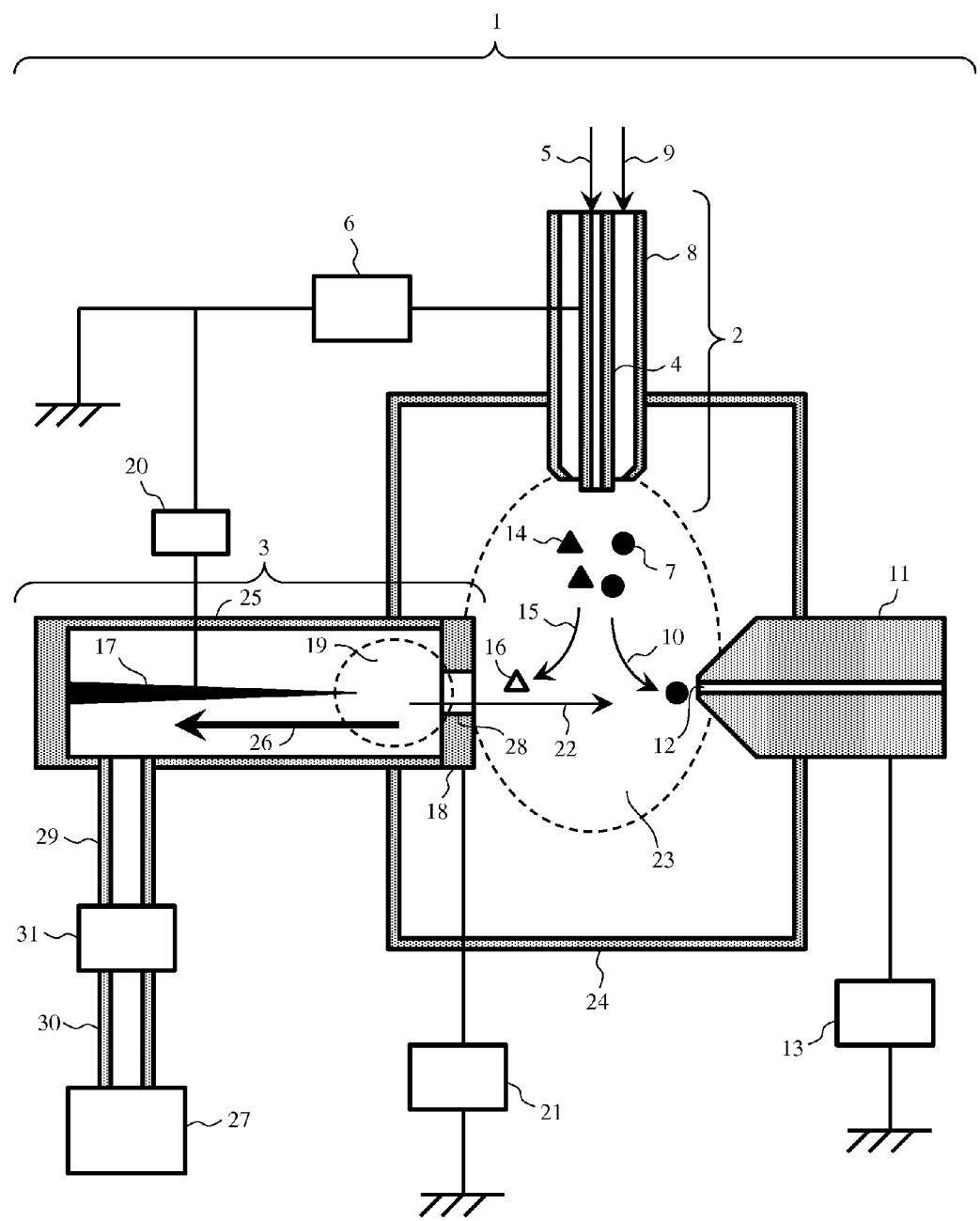
FIG. 17 illustrates a configuration of a hybrid ion source according to Embodiment 15.

FIG. 17 schematically illustrates the configuration of a hybrid ion source 1 according to the present embodiment. The basic configuration of the hybrid ion source 1 in the present embodiment is similar to that of FIG. 1. In FIG. 17, the same reference numerals are assigned to elements corresponding to FIG. 1, and the following describes differences only.

The present embodiment includes a power source 6, a power source 13, a power source 20 and a power source 21 that are equipped with a function of switching the voltage applied rapidly. The power source 6 applies voltage to the capillary 4, the power source 13 applies voltage to the first aperture electrode 11, the power source 20 applies voltage to the needle electrode 17, and the power source 21 applies voltage to the counter electrode 18. A controller 45 not illustrated switching-controls the voltage of these power sources.

Figure 18:
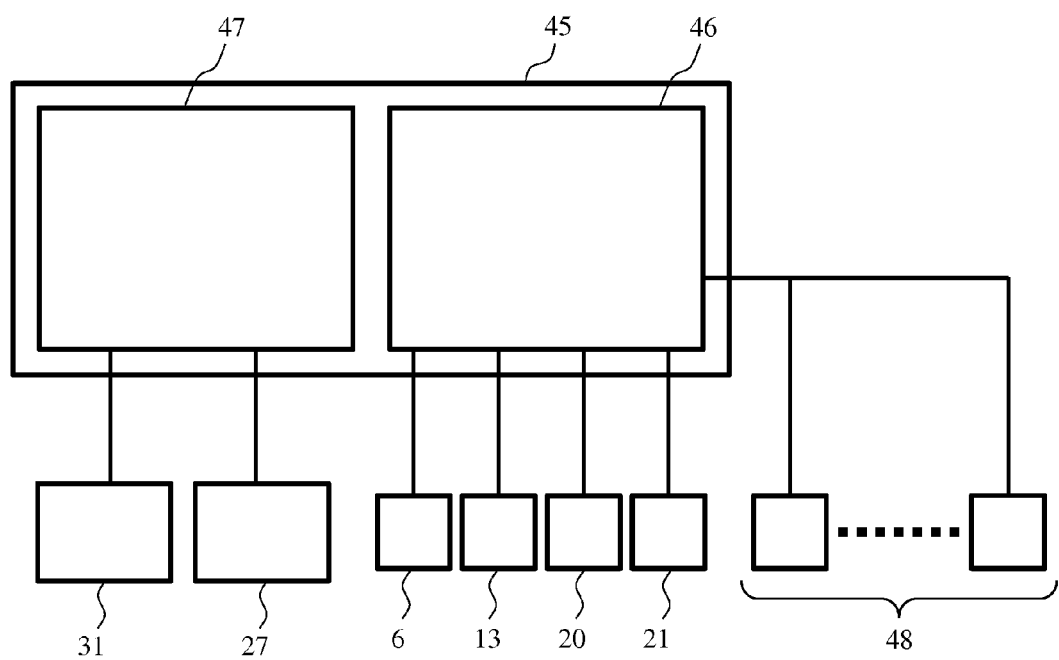
FIG. 18 describes a control system for the hybrid ion source according to Embodiment 15.

FIG. 18 illustrates the functional configuration of the controller 45 and the connection relationship of each functional unit and units to be controlled. The controller 45 includes a voltage control unit 46 and a gas flow rate control unit 47. The voltage control unit 46 controls the voltage applied from the power source 6, the power source 13, the power source 20 and the power source 21. The gas flow rate control unit 47 controls the operations of the exhaust pump 27 and the flow-rate adjustment mechanism 31.

As described above, both of the ESI ion source 2 and the APCI ion source 3 can generate positive ions and negative ions. The voltage condition to apply various electrodes, however, varies with the polarity of ions to be generated. Basically, in order to generate positive ions, positive voltage is applied to these electrodes, and in order to generate negative ions, negative voltage is applied to these electrodes. The condition to apply voltage, however, is not limited to this.

In order to ionize the sample solution 5 continuously flowing in both of positive and negative ionization modes, the power sources have to be switched rapidly.

The hybrid ion sources 1 according to the above-stated embodiments generate APCI ions in the state where the air flow 26 from the ESI ionization area 23 to the corona discharge area 19 is present, and the optimum flow speed condition may be different depending on whether positive ions or negative ions are to be generated. That is, the flow speed may be switched between positive ions and negative ions.

Then, the controller 45 controls the operations of the exhaust pump 27 and the flow-rate adjustment mechanism 31 in response to the switching timing of each power source so as to satisfy the optimum flow-speed condition. This can prevent the lowering of ion intensity due to positive/negative mode switching.

When the electrode 39 is included as in FIG. 9, FIG. 11, FIG. 12, FIG. 14 and FIG. 16, voltage applied to this electrode also has to be switching-controlled. Voltage applied to other electrodes, if any, or to an internal electrode in a mass spectrometer to analyze ions also has to be switching-controlled. FIG. 18 illustrates these electrodes collectively as a power source 48.

When direct exhaust of the ESI ionization chamber 24 is performed by the exhaust pump 41 or the flow-rate adjustment mechanism 44 is provided as in FIG. 11, the exhaust pump 41 and the flow-rate adjustment mechanism 44 also can be controlled at the same time.

In addition to the basic effects from Embodiment 1, the hybrid ion source of the present embodiment can optimize the applied voltage and the flow speed condition in response to switching of ionization modes. The configuration of the device of the present embodiment may be combined with Embodiments 1 to 14 as described above for use.

Embodiment 16

The present embodiment describes a hybrid ion source having a substantially similar configuration to Embodiment 1, where a pipe is added to introduce organic solvent to the APCI ion source.

Figure 19:
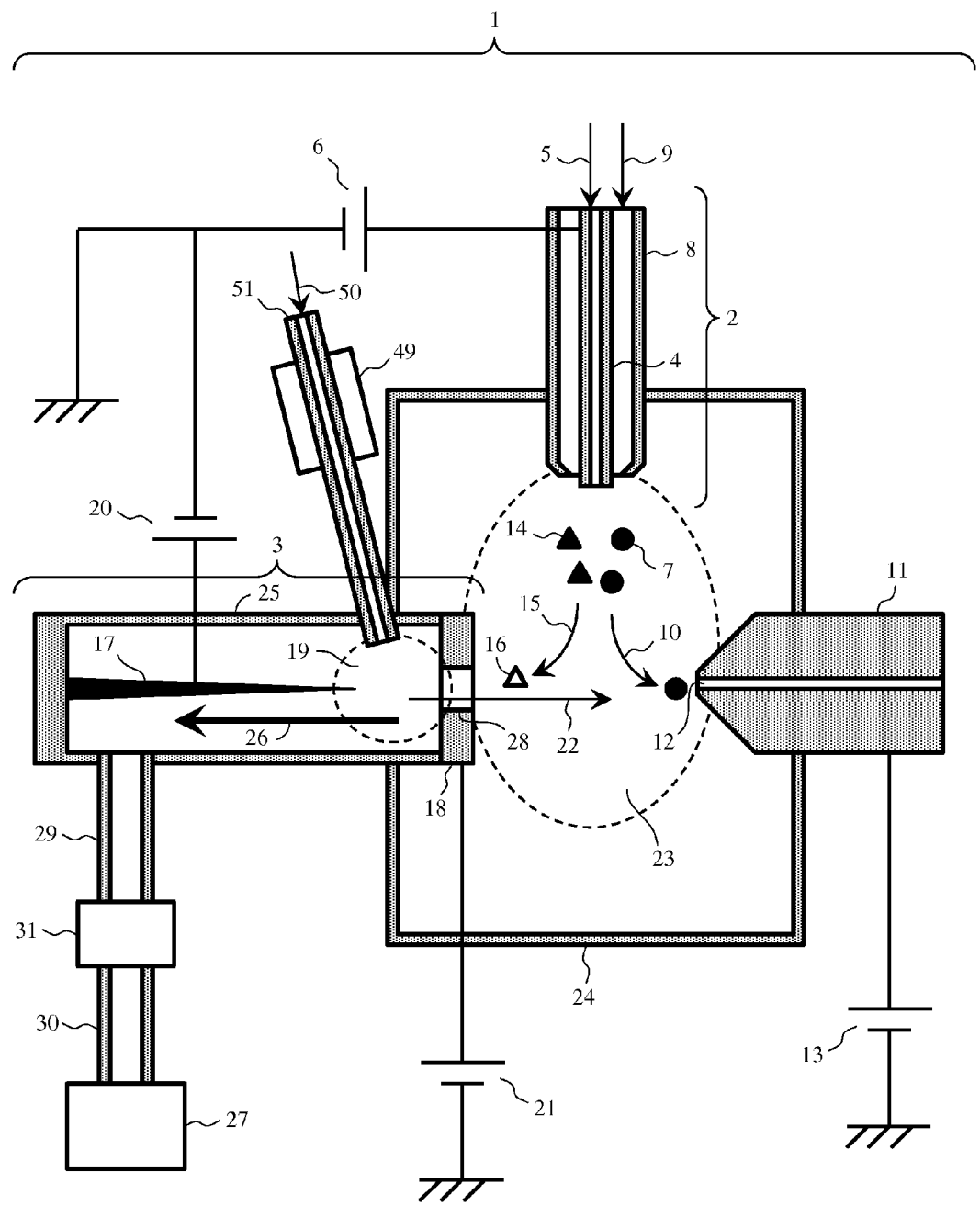
FIG. 19 illustrates a configuration of a hybrid ion source according to Embodiment 16.

FIG. 19 schematically illustrates the configuration of a hybrid ion source 1 according to the present embodiment. The basic configuration of the hybrid ion source 1 in the present embodiment is similar to that of FIG. 1. In FIG. 19, the same reference numerals are assigned to elements corresponding to FIG. 1, and the following describes differences from Embodiment 1 only.

The present embodiment is configured so that a pipe 51 is attached toward the corona discharge area 19 formed inside of the APCI ion source 3. A heating unit 49 is disposed around the circumference of the pipe 51, and so organic solvent 50 introduced into the pipe 51 is heated by the heating unit 49 for vaporization. The vaporized organic solvent 50 is introduced as gas to the corona discharge area 19.

Such a configuration is used because the sample solution 5 containing mixture of organic solvent, water and the like is introduced to the ESI ion source 2 in some cases. When such organic solvent containing water is used, generation efficiency of primary ions at the APCI ion source 3 may be lowered. Then, as illustrated in FIG. 19, the present embodiment is configured so that gas generated from the organic solvent 50 is directly introduced to the APCI ion source 3 via the pipe 51. This can increase the density of organic solvent at the corona discharge area 19 (lowering the density of water and the like), and can generate a large amount of primary ions. As a result, generation efficiency of APCI ions can be improved.

The heating unit 49 may have various heating schemes, such as heating using a heat block so as to directly come into contact with the pipe 51, or heating using a lamp or infrared rays so as to heat the pipe 51 in a non-contact manner.

The present embodiment can provide a hybrid ion source 1 achieving high generation efficiency of APCI ions when mixture solution containing organic solvent, water and the like is used as the sample solution 5 as stated above as well. The configuration of the present embodiment may be combined with the configuration of Embodiments 1 to 15 as stated above for use.

Embodiment 17

The present embodiment describes a mass spectrometer including a hybrid ion source according to Embodiment 1.

Figure 20:
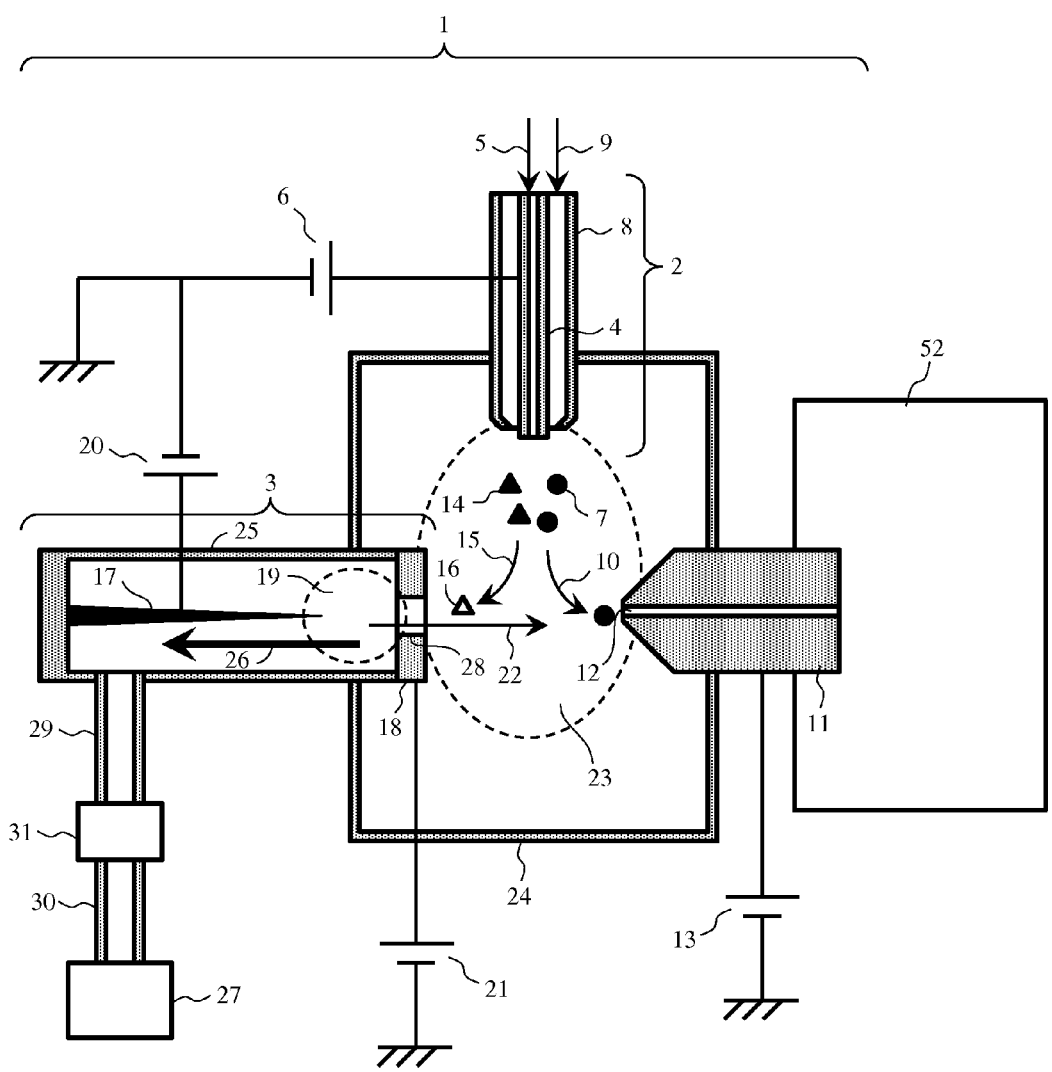
FIG. 20 illustrates a configuration of a mass spectrometer according to Embodiment 17.

FIG. 20 illustrates an exemplary configuration of the mass spectrometer according to the present embodiment. In the mass spectrometer illustrated in FIG. 20, the hybrid ion source 1 has the configuration similar to that of FIG. 1. In FIG. 20, the same reference numerals are assigned to elements corresponding to FIG. 1, and the following describes differences from Embodiment 1 only.

The mass spectrometer in the present embodiment includes a mass spectrometry/detection unit 52 coupled with one end side of the first aperture electrode 11. That is, both of the ESI ions 7 and the APCI ions generated at the hybrid ion source 1 are introduced to the mass spectrometry/detection unit 52 at the same time. The mass spectrometry/detection unit 52 analyzes the mass and the structure of ions introduced in details through the process such as separation and dissociation of the ions. As a result, mass spectrometry can be conducted precisely and in a short time with one measurement. Herein analysis procedure is executed by a data processing unit (calculator) not illustrated.

Note that various schemes can be used for the mass spectrometry, such as quadrupole mass spectrometry, ion trap, and time-of-flight mass spectrometry. These schemes may be combined for use.

Although the present embodiment includes the hybrid ion source 1 according to Embodiment 1, the mass spectrometer may be configured by combining the hybrid ion source 1 according to Embodiments 2 to 16 and the mass spectrometry/detection unit 52.

Embodiment 18

The present embodiment describes an ion mobility spectrometer including a hybrid ion source according to Embodiment 1.

Figure 21:
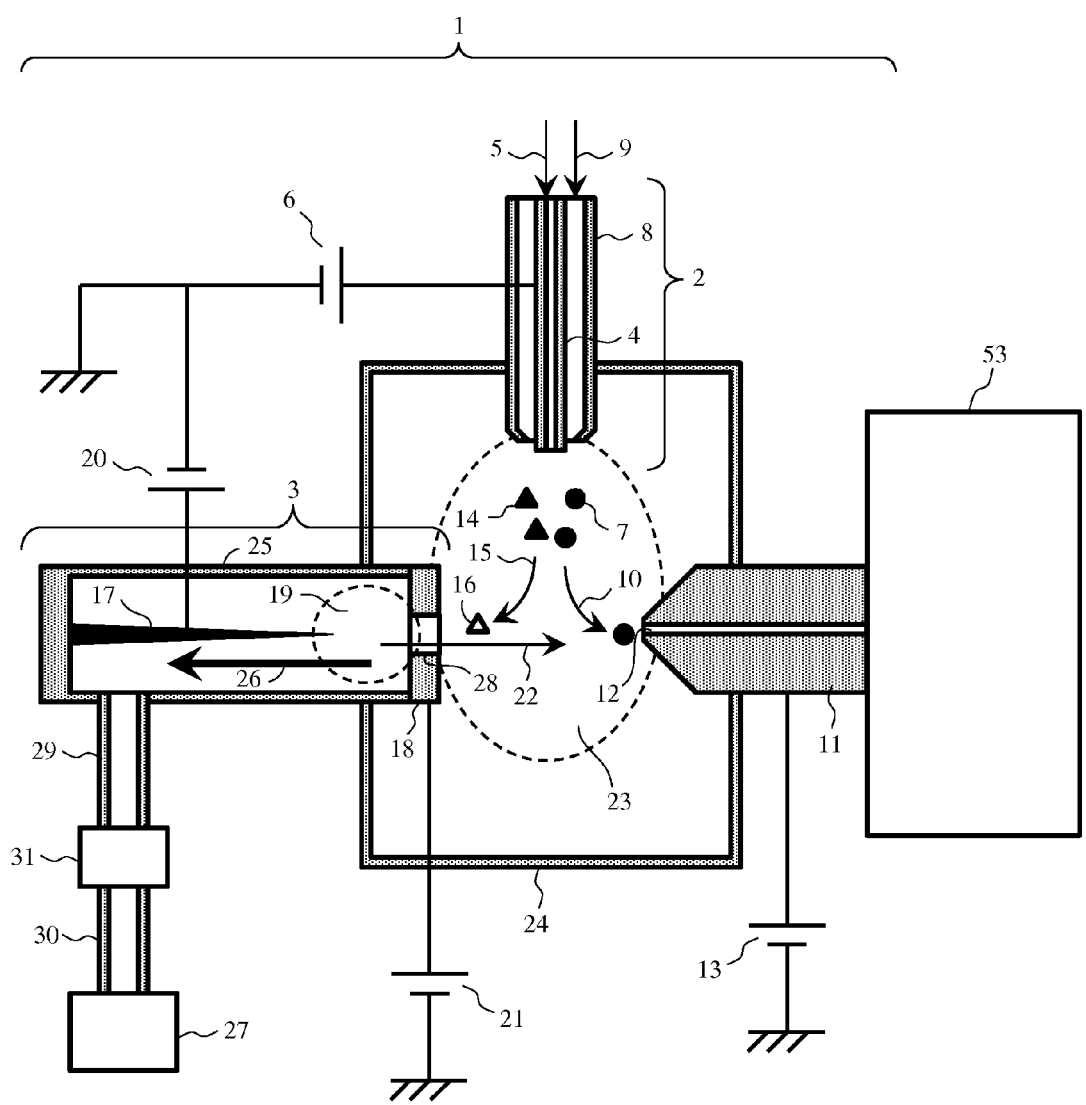
FIG. 21 illustrates a configuration of an ion mobility spectrometer according to Embodiment 18.

FIG. 21 illustrates an exemplary configuration of the ion mobility spectrometer according to the present embodiment. In the ion mobility spectrometer illustrated in FIG. 21, the hybrid ion source 1 has the configuration similar to that of FIG. 1. In FIG. 21, the same reference numerals are assigned to elements corresponding to FIG. 1, and the following describes differences from Embodiment 1 only.

The ion mobility spectrometer in the present embodiment includes an ion mobility unit 53 coupled with one end side of the first aperture electrode 11. That is, both of the ESI ions 7 and the APCI ions generated at the hybrid ion source 1 are introduced to the ion mobility unit 53 at the same time. The ion mobility unit 53 separates ions based on a difference in mobility resulting from the ion structure for analysis.

The ion mobility unit 53 may be based on various schemes, such as a drift tube scheme and a parallel-plate scheme. These schemes may be combined for use. The ion mobility unit 53 of the present embodiment may be combined with the mass spectrometry/detection unit 52 as stated above for use.

Although the present embodiment includes the hybrid ion source 1 according to Embodiment 1, the ion mobility spectrometer may be configured by combining the hybrid ion source 1 according to Embodiments 2 to 16 and the ion mobility unit 53.

Embodiment 19

The present embodiment describes another exemplary configuration of a hybrid ion source. The embodiments as stated above include a hybrid ion source having the ESI ion source 2 and the APCI ion source 3, and the present embodiment describes a hybrid ion source including a first ion source to mainly ionize a solution sample and a second ion source to mainly ionize a gas sample such as gas.

Figure 22:
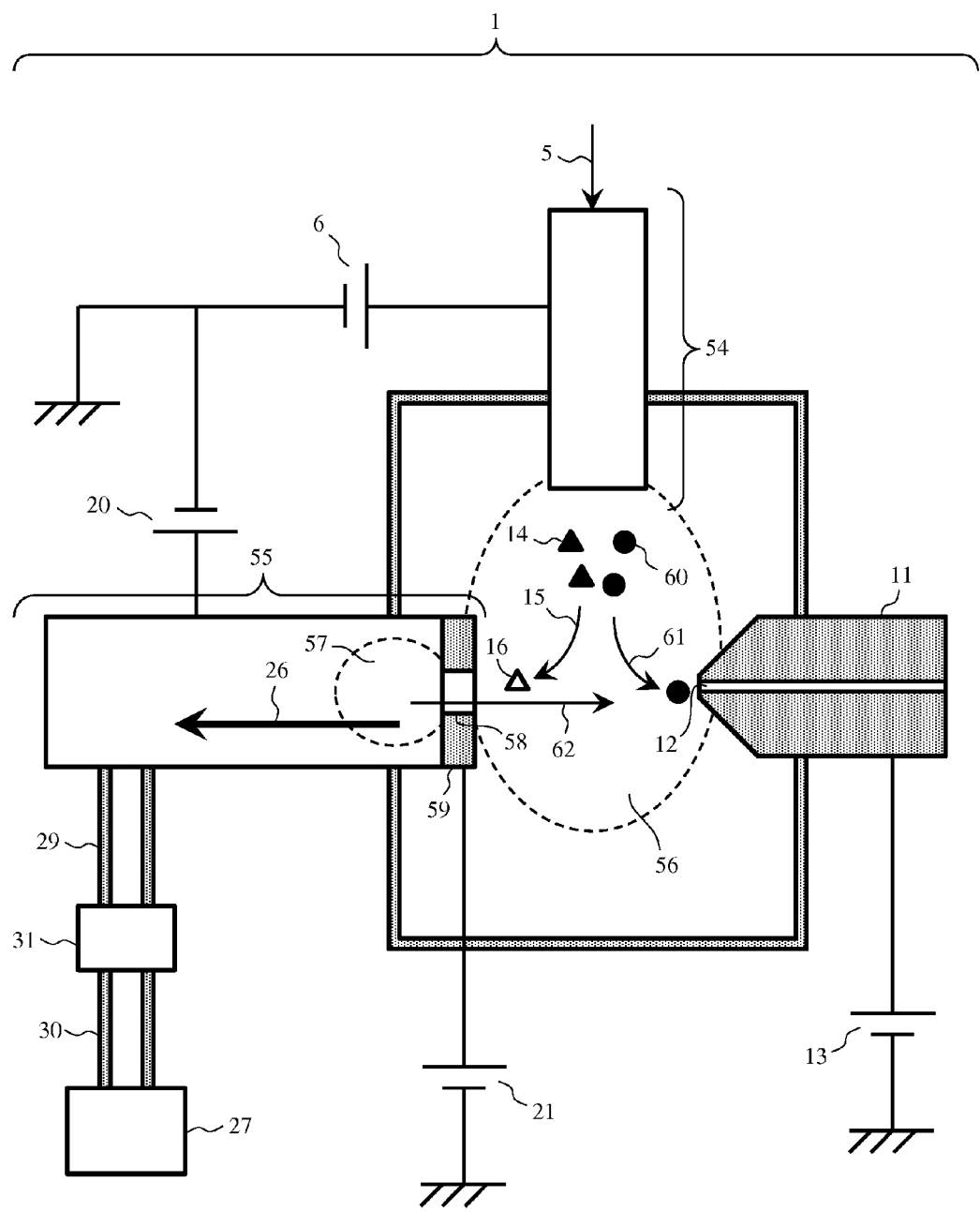
FIG. 22 illustrates a configuration of a hybrid ion source according to Embodiment 19.

FIG. 22 schematically illustrates a configuration of a hybrid ion source 1 according to the present embodiment. The basic configuration of the hybrid ion source 1 in the present embodiment is similar to that of FIG. 1. In FIG. 22, the same reference numerals are assigned to elements corresponding to FIG. 1, and the following describes differences from Embodiment 1 only.

The present embodiment includes a first ion source 54 to mainly ionize a solution sample, and a second ion source 55 to mainly ionize a gas sample such as gas, which are attached to a chamber. In the case of the present embodiment as well, the first ion source 54 is attached to the ceiling face of the chamber, and the second ion source 55 is attached to a side-wall face of the chamber so as to be opposed to the first aperture electrode 11.

The ESI ion source 2 may be used for the first ion source 54, which may be based on various ionization schemes, such as thermospray ionization (TSP), sonic spray ionization (SSI), cold spray ionization (CSI), laser spray ionization (LSI), and desorption electrospray ionization (DESI).

The APCI ion source 3 may be used for the second ion source 55, which may be based on various ionization schemes, such as atmospheric pressure photonization (APPI), and dielectric barrier discharge ionization (DBD).

These ionization schemes as stated above that can be used for the first ion source 54 and the second ion source 55 are just examples, and many other various ionization schemes can be used therefor.

In the present embodiment, a first ionization area 56 where ions are generated by the first ion source 54 and a second ionization area 57 where ions are generated by the second ion source 55 are physically divided by an electrode 59 having an opening 58.

In the case of the present embodiment as well, the exhaust pump 27 is connected to the second ion source 55 to mainly ionize a gas sample, so as to generate the air flow 26 in the direction from the first ionization area 56 to the second ionization area 57. This allows the sample gas 16 generated at the first ionization area 56 to be introduced to the second ionization area 57 effectively. As a result, intensity of ions generated at the second ion source 55 can be improved.

In the case of the present embodiment, the electrode 59 has electrical potential set at the electrical potential applied from the power source 21. This can reduce not only the influences from the electric field generated at the first ion source 54 on the second ionization area 57 but also the influences from the electric field generated at the second ion source 55 on the first ionization area 56. As a result, the first ion source 54 and the second ion source 55 are allowed to prevent the lowering of intensity of ions generated by the mutual ion sources.

Ions 60 generated at the first ion source 54 pass along the orbit of arrow 61, for example, and are introduced to the opening 12 of the first aperture electrode 11. Ions generated at the second ion source 55 pass along the orbit of arrow 62, for example, and are introduced to the opening 12 of the first aperture electrode 11.

The configuration of the device of the present embodiment may be combined with Embodiments 1 to 18 as described above for use.

Other Embodiments

The present invention is not limited to the above-described embodiments, and may include various modification examples. For instance, the entire detailed configuration of the embodiments described above for explanatory convenience is not always necessary for the present invention. A part of one embodiment may be replaced with the configuration of another embodiment, or the configuration of one embodiment may be added to the configuration of another embodiment. The configuration of each embodiment may additionally include another configuration, or a part of the configuration may be deleted or replaced. A pump described in the present specification as exhaust means may be one that can generate air flow, which may be a fan or the like, instead of the pump.

Control lines and information lines shown are those required for description, and all of the control line and information lines of a product are not always illustrated. It can be considered that in an actual product, almost all configurations are mutually connected.

REFERENCE SIGNS LIST

1 Ion source
2 ESI ion source
3 APCI ion source
4 Capillary
5 Sample solution
6 Power source
7 ESI ions
8 Spray pipe
9 Nebulizer gas
11 First aperture electrode
12 Opening
13 Power source
14 Droplet
16 Sample gas
17 Needle electrode
18 Counter electrode
19 Corona discharge area
20 Power source
21 Power source
23 ESI ionization area
24 ESI ionization chamber
25 Corona discharge chamber
26 Air flow
27 Exhaust pump
28 Opening
29 Pipe
30 Pipe
31 Flow-rate adjustment mechanism
32 Heating unit
33 Heating unit
34 Heating unit
35 Heating unit
37 Heating gas pipe
38 Heating gas
39 Electrode
40 Gas
41 Exhaust pump
42 Pipe
43 Pipe
44 Flow-rate adjustment mechanism
45 Controller
46 Voltage control unit
47 Gas flow rate control unit
48 Power source
49 Heating unit
50 Organic solvent
51 Pipe
52 Mass spectrometry/detection unit
53 Ion mobility unit
54 First ion source
55 Second ion source
56 First ionization area
57 Second ionization area
58 Opening
59 Electrode
60 Ion

The invention claimed is:

1. A hybrid ion source, comprising:
a first chamber;
a first ion source to generate first ions and to spray droplets or a gas component of a sample solution for ionization;
a second ion source to generate second ions by ionizing the droplets or the gas component sprayed from the first ion source; and
an aperture electrode disposed to introduce the first and second ions generated by the respective first and second ion sources into a detection unit,
wherein the second ion source includes:
an opening between a first ionization area, in which the first ions are generated, and a second ionization area, in which the second ions are generated, to introduce the droplets or the gas component into the second ionization area and to emit the second ions from the second ion source, and
first exhaust means for generating an air flow in a direction from the first ionization area towards the second ionization area.

2. The hybrid ion source according to claim 1,
wherein the first ion source includes a capillary electrode to spray the sample solution,
wherein the second ion source includes a needle electrode, and a counter electrode disposed at a position opposite to the needle electrode,
wherein the counter electrode includes the opening, and
wherein an intensity of an electric field between the counter electrode and the capillary electrode is less than an intensity of an electric field between the aperture first electrode and the capillary electrode.

3. The hybrid ion source according to claim 1, further comprising:
a heating unit for heating the first ionization area.

4. The hybrid ion source according to claim 1, further comprising:
a heating unit for heating the second ionization area.

5. The hybrid ion source according to claim 1,
wherein the second ion source includes a needle electrode,
wherein the second ion source includes a counter electrode disposed at a position opposed to the needle electrode, and
wherein the second ion source includes a heating unit for heating the needle electrode.

6. The hybrid ion source according to claim 1,
wherein the first ion source includes a capillary electrode to spray the sample solution, and
wherein the hybrid ion source further includes a heating unit disposed at a position opposed to the capillary electrode for heating the droplets or the gas component sprayed from the capillary electrode.

7. The hybrid ion source according to claim 1, further comprising:
second exhaust means connected to the chamber for exhausting the chamber.

8. The hybrid ion source according to claim 2,
wherein the opening of the counter electrode comprises a plurality of openings.

9. The hybrid ion source according to claim 1,
wherein the second ion source comprises a plurality of second ion sources.

10. The hybrid ion source according to claim 1,
wherein the first ion source includes a capillary electrode to spray the sample solution, and
wherein the hybrid ion source further includes:
at least one of a first power source to apply a first voltage to the capillary electrode and a second power source to apply a second voltage to a needle electrode in the second ion source; and
a controller that controls a flow rate for exhaust of the first exhaust means in synchronization with a timing to switch at least one of the applied first and second voltages at the at least one of the first and the second power sources.

11. The hybrid ion source according to claim 1, further comprising:
a pipe to introduce a solvent into the second ionization area.

12. The hybrid ion source according to claim 1,
wherein the first ion source is an electrospray ionization (ESI) ion source, and
wherein the second ion source is an atmospheric pressure chemical ionization (APCI) ion source.

13. A mass spectrometer, comprising:
the hybrid ion source according to claim 1; and
a mass spectrometry unit, which is the detection unit to which the first and second ions are introduced from the aperture electrode.

14. An ion mobility spectrometer, comprising:
the hybrid ion source according to claim 1; and
an ion mobility unit which is the detection unit to which the first and second ions are introduced from the aperture electrode.

15. A hybrid ion source, comprising:
a chamber;
a first ion source to generate first ions and to spray droplets or a gas component of a sample solution for ionization;
a second ion source to generate second ions by ionizing the droplets or the gas component sprayed from the first ion source; and
an aperture electrode disposed to introduce the first and second ions generated by the respective first and second ion sources to outside the chamber;
wherein the second ion source includes:
an opening between a first ionization area, in which the first ions are generated, and a second ionization area, in which the second ions are generated, to introduce the droplets or the gas component into the second ionization area and to emit the second ions from the second ion source, and
first exhaust means for generating an air flow in a direction from the first ionization area towards the second ionization area,
wherein the first ion source includes a capillary electrode to spray the droplets or the gas component of the sample solution,
wherein the second ion source includes a needle electrode disposed at a position opposite the opening, and
wherein the hybrid ion source further includes:
at least one of a first power source to apply a first voltage to the capillary electrode and a second power source to apply a second voltage to the needle electrode in the second ion source; and
a controller that controls a flow rate for exhaust of the first exhaust means in synchronization with a timing to switch at least one of the applied first and second voltages at the at least one of the first and the second power sources.

16. The hybrid ion source according to claim 15,
wherein the second ion source includes a counter electrode having the opening disposed at a position opposite to the needle electrode, and
wherein an intensity of an electric field between the counter electrode and the capillary electrode is less than an intensity of an electric field between the aperture electrode and the capillary electrode.

17. The hybrid ion source according to claim 15, further comprising:
a heating unit for heating the first ionization area.

18. The hybrid ion source according to claim 15, further comprising:
a heating unit for heating the second ionization area.

19. The hybrid ion source according to claim 15, further comprising:
second exhaust means connected to the chamber for exhausting the chamber.

20. The hybrid ion source according to claim 15,
wherein the second ion source comprises a plurality of second ion sources.

* * * * *